United States Patent
Lee et al.

(10) Patent No.: US 11,242,321 B2
(45) Date of Patent: Feb. 8, 2022

(54) SALT FORMS OF ORGANIC COMPOUND

(71) Applicant: KAINOS MEDICINE INC., Seongnam-si (KR)

(72) Inventors: Jae Moon Lee, San Diego, CA (US); Sungeun Yoo, Sejong (KR); Sunmi Shin, Seongnam-si (KR)

(73) Assignee: Kainos Medicine Inc., Seongnam-Si (KR)

( * ) Notice: Subject to any disclaimer, the term of this patent is extended or adjusted under 35 U.S.C. 154(b) by 0 days.

(21) Appl. No.: 16/965,544

(22) PCT Filed: Jan. 30, 2019

(86) PCT No.: PCT/US2019/015890
§ 371 (c)(1),
(2) Date: Jul. 28, 2020

(87) PCT Pub. No.: WO2019/152546
PCT Pub. Date: Aug. 8, 2019

(65) Prior Publication Data
US 2021/0047279 A1 Feb. 18, 2021

Related U.S. Application Data

(60) Provisional application No. 62/623,974, filed on Jan. 30, 2018.

(51) Int. Cl.
*C07D 231/40* (2006.01)

(52) U.S. Cl.
CPC .................. *C07D 231/40* (2013.01)

(58) Field of Classification Search
CPC .................................................. C07D 231/40
USPC ....................................................... 548/372.5
See application file for complete search history.

(56) References Cited

U.S. PATENT DOCUMENTS 7,939,550 B2  5/2011  Jung et al.

FOREIGN PATENT DOCUMENTS

WO  2006/127595 A1  11/2006

OTHER PUBLICATIONS

PharmTech (2006) vol. 30(10), pp. 1-17.*
Handbook of Pharmaceutical Salts; Properties, Selection and Use (2011), Stall and Wermuth, Eds. Chap. 5.*
Handbook of Pharmaceutical Salts; Properties, Selection and Use (2011), Stall and Wermuth, Eds. Chap. 6.*
Office Action for related European Patent Application No. 19748229.2-1110, dated May 27, 2021, 7 pages.
Kumar et al., "An overview of automated systems relevant in pharmaceutical salt screening", Drug Discovery Today, vol. 12, Issues 23-24, Dec. 2007, pp. 1046-1053.
Berge et al., "Pharmaceutical Salts", Journal of Pharmaceutical Sciences, American Chemical Society and American Pharmaceutical Associations, US, vol. 66, No. 1, Jan. 1, 1977, pp. 1-19.
Wang et al., Pharmacological possibilities for protection against myocardial reperfusion injury; Cardiovascular Research 55 (2002) 25-37.
Hearse, Myocardial protection during ischemia and reperfusion; Molecular and Cellular Biochemistry 186: 177-184, 1998.
Liu, Ischemia-Reperfusion-Related Repair Deficit after Oxidative Stress: Implications of Faulty Transcripts in Neuronal Sensitivity after Brain Injury; J Biomed Sci 2003;10:4-13.
Lipton, Ischemic Cell Death in Brain Neurons; Physiological Reviews, vol. 79, No. 4, Oct. 1999.
Renolleau et al, A model of transient unilateral focal ischemia with reperfusion in the P7 neonatal rat: morphological changes indicative of apoptosis; Stroke, American Heart Association, 1998, 29 (7), pp. 1454-1460; discussion 1461. HAL Id: inserm-00482495.
Webster et al., Hypoxia-activated apoptosis of cardiac myocytes requires reoxygenation or a pH shift and is independent of p53; J Clin Invest. 1999;104(3):239-252. https://doi.org/10.1172/JCI5871.
Katus et al., Detection of Myocardial Cell Damage in Patients with Unstable Angina by Serodiagnostic Tools, (1990).
Vandeplassche et al., Ultrastructural damage and Ca2+-shifts in the canine myocardium subjected to regional incomplete ischemia; Basic Res Cardiol 85:384-391 (1990).
Napper et al., Reduced glutamate uptake by retinal glial cells under ischemic0hypoxic conditions; Visual Neuroscience (1999), 16, 149-158.
Yrjanheikki et al, A tetracycline derivative, minocycline, reduces inflammation and protects against focal cerebral ischemia with a wide therapeutic window; 13496-13500, PNAS, Nov. 9, 1999, vol. 96, No. 23.
Scarabelli et al., Minocycline Inhibits Caspase Activation and Reactivation, Increases the Ratio of XIAP to Smac/DIABLO, and Reduces the Mitochondrial Leakage of Cytochrome C and Smac/DIABLO; Journal of the American College of Cardiology, vol. 43, No. 5, 2004.
Wang et al., Minocycline Up-regulates Bcl-2 and Protects against Cell Death in Mitochondria, The Journal of Biological Chemistry, vol. 279, No. 19, Issue of May 7, pp. 19948-19954, 2004.
Zoppo et al, Trends and Future Developments in the Pharmacological Treatment of Acute Ischaemic Stroke; Drug s 1997 Jut 54 ( I); 9-38.
Sziraki et al., Manganese: A Transition Metal Protects Nigrostriatal Neurons From Oxidative Stress in the Iron-Induced Animal Model of Parkinsonism; Neuroscience vol. 85, No. 4, pp. 1101-1111, 1998.
International Search Report and Written Opinion issued in the corresponding Application No. PCT/US2019/015890 dated Apr. 16, 2019.
Remington: the Science and Practice of Pharmacy, 22nd Ed., c. 2013 by Pharmaceutical Press.

(Continued)

*Primary Examiner* — Taofiq A Solola
(74) *Attorney, Agent, or Firm* — Ditthavong, Steiner & Mlotkowski

(57) ABSTRACT

A salt compound of 4-(2-((4-bromophenyl)thio)acetamido)-1-phenethyl-1H-pyrazole-3-carboxylic acid is disclosed. Also disclosed are methods for making the salt compound and formulations of the salt compound into dosage forms for clinical use.

16 Claims, 36 Drawing Sheets

(56) References Cited

OTHER PUBLICATIONS

Katz, A. M. et al., J. Mol Cell. Cardiol.2:11-20, 1985.
Saegesser, F. et al., Pathobiology Annual 1979, vol. 9, pp. 303-337.
Ferrari R., Ischaemic heart disease: clinical improvement with metabolic approach; Rev Port Cardiol. Nov. 2000; 19 Suppl 5:V7-20.
Jeong et al, Subacute toxicity evaluation of KR-33493, FAF1 inhibitor for a new anti-parkinson's disease agent, after oral administration in rats and dogs; Regulatory Toxicology and Pharmacology 81 (2016) 387-396.

* cited by examiner

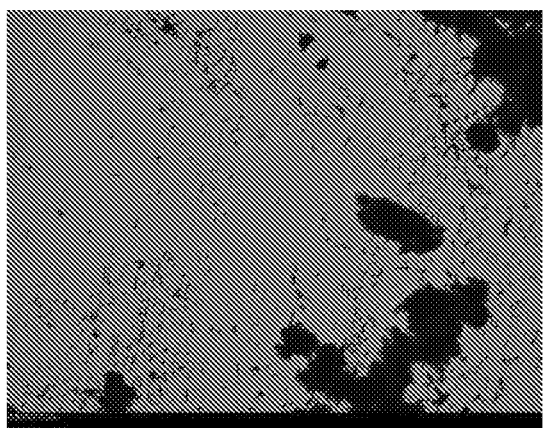
Figure 29A
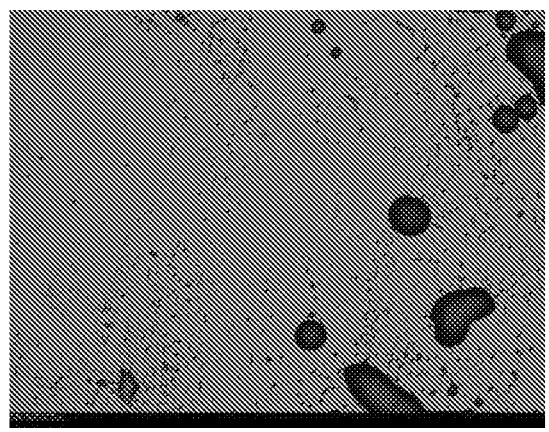
Figure 29B
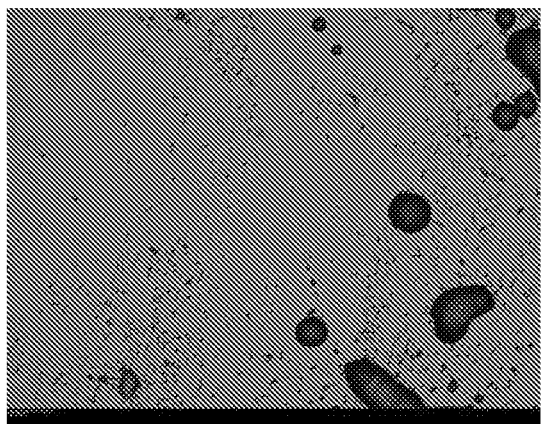
Figure 29C
Figure 30
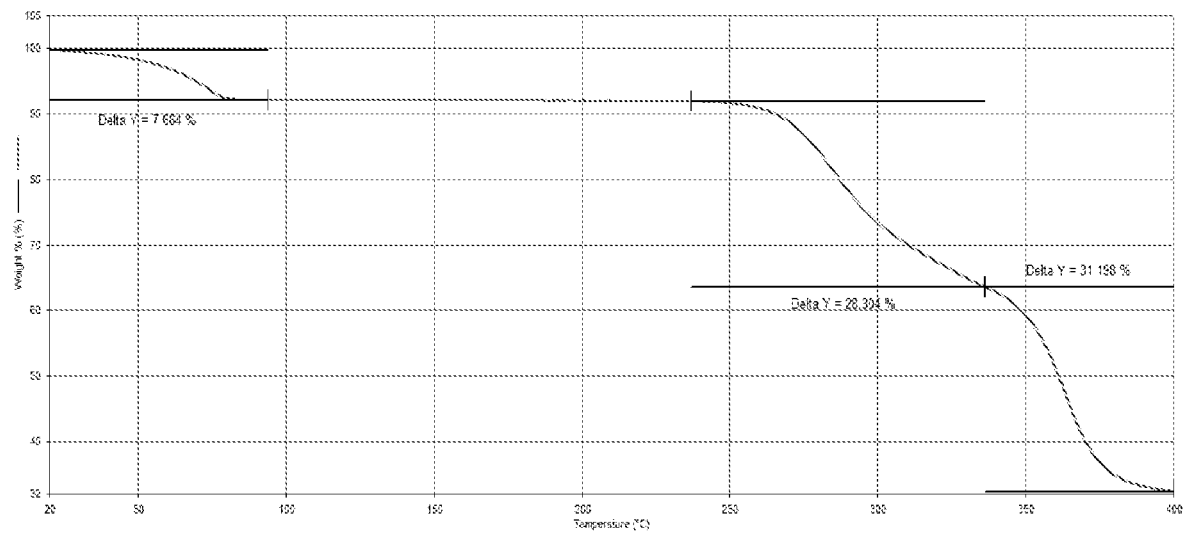

XRPD pattern 1

XRPD pattern 2

XRPD pattern 3

XRPD pattern 4

XRPD pattern 5

NMR pattern 1

NMR pattern 2

NMR pattern 3

NMR pattern 4

NMR pattern 5

SALT FORMS OF ORGANIC COMPOUND

FIELD

The disclosure relates to various formulations and compositions comprising a salt compound useful as an inhibitor of FAF-1. Also disclosed are methods for preparing the salt compound.

BACKGROUND

Ischemia means a reduction in blood flow to organs, tissues or a region thereof, caused by contraction or occlusion of one or more blood vessels. Once ischemia occurs, even if reperfusion is prompt, it is followed by various sequelae that develop due to damage of nerve cells. Such ischemia frequently occurs in coronary artery diseases, cardiovascular diseases, angina pectoris, headache or other symptoms related to blood vessel occlusion or contraction, and eventually leads to irreversible damage, i.e., necrosis of cells or tissues.

Since ischemic diseases such as myocardial infarction, arrhythmia or heart failure caused by cell damage and dysfunction during ischemia-reperfusion have a high morbidity rate, a high mortality rate, and a low complete cure rate, basic research and clinical studies have been ongoing in this field for fifty years [Wang, Q. D. et al., Cardiovasc. Res. 55:25-37, 2002]. Especially, since ischemia-reperfusion injury involves various physiological mechanisms including change of metabolism, immune response and ion homeostasis, generation of oxygen free radicals and the like, studies are ongoing in various fields related to immune modulators, cell death suppressors, ion channel modulators, etc. [Hearse, D. J. et al., Mol. Cell. Biochem. 186:177-184, 1998]. Based on such mechanistic research, there have so far been developed a number of therapeutics and surgical operations focused on novel acting sites, but no technique for protecting cardiomyocytes from ischemia-reperfusion injury has yet been commercialized. Therefore, there is a need for an agent for preventing and treating ischemic heart diseases or a heart protecting agent, which can delay the progress of ischemic damage of cardiomyocytes and reduce reperfusion-induced injuries.

In addition, it has become plain that if ischemia is relieved by recovery of blood flow, the generation of reactive oxygen species (ROS) is accelerated, which causes a remarkable decrease of glutathione and brings about more serious diseases. Similar diseases are observed when blood flow stops or recovers during various techniques of transplant surgery of various kinds of organs such as heart, liver, lung, pancreas or blood vessels, and will be a problem in incising and removing an organ as well. Reactive oxygen and reactive free radicals assumed to cause diseases are detected in the cytoplasm and organelles of cells of tissues, especially in mitochondria producing ATP as a main energy source of a cell. In mitochondria, it is observed that the above reactive molecules are mainly released through a respiratory chain, and their concentration is significantly increased during ischemia-reperfusion.

In this regard, since ischemia leads to cell death or necrosis of cells, and especially cell death occurring after reperfusion is a main cause of tissue damage, ischemic cell death is a cause for various ischemic diseases, for example brain ischemia, heart ischemia, diabetic cardiovascular disease, heart failure, myocardial hypertrophy, retinal ischemia, ischemic colitis and ischemic acute renal failure.

In brain ischemia, the depletion of an energy source due to the reduction of blood supply induces ischemic cell death. Then, the ischemic cell death excessively activates a cell membrane receptor, which is followed by various biochemical alterations including accumulation of glutamic acid and calcium, respectively outside and inside of cells, and damage of lipids, proteins and nucleic acids, and finally leads to brain tissue injury (Liu, P. K., J. Biomed. Sci. 10:4-13, 2003; Lipton, P., Physiol. Rev. 79:1431-1568, 1999; and Renolleau, S. et al., Stroke 29:1454-1460, 1998).

In cases of myocardial infarction, heart failure and arrhythmia as ischemic heart diseases, it has been reported that ischemic cell death occurs by activation of lipid enzymes triggering damage to cell membranes, and subsequent changes of pH and calcium transport [Ferrari, R. Rev. Port. Cardiol. 5:7-20, 2000; Webster, K. A. et al., J. Clin. Invest. 104:239-252, 1999; Katz, A. M. et al., J. Mol Cell. Cardiol. 2:11-20, 1985; and Vandeplassche, G. et al., Basic Res. Cardiol. 85:384-391, 1990]. In retinal ischemia, it has been known that cell death of retinal cells mediated by glutamate is mediated by ischemic cell death [Napper, G. A. et al., Vis. Neurosci. 16:149-158, 1999]. Insufficient blood supply to colon causes ischemic cell death, and then, occlusive injury of arteries due to cell necrosis and hemodynamic disorders lead to ischemic colitis as an ischemic disease [Saegesser, F. et al., Pathobiol. Annu. 9:303-337, 1979].

Meanwhile, Minocycline, which is one of the tetracycline antibiotics inhibiting ischemic cell death, has been known to be effective in ischemic diseases such as cerebral infarction [Yrjanheikki, J. et al., Proc. Natl. Acad. Sci. USA 96:13496-13500, 1999], myocardial infarction [Scarabelli, T. M. et al., J. Am. Coll. Cardiol. 43:865-874, 2004] and an ischemic acute renal failure [Wang, J. et al., J. Biol. Chem. 279:19948-19954, 2004], suggesting that ischemic cell death is a cause of the above diseases.

Further, it has been known that damage or cell death of nerve cells induced by ischemia is a main cause of various nervous system diseases such as Alzheimer's disease, Parkinson's disease, glaucoma and diabetic neuropathy, and of pathologies resulting from stroke, head trauma, neonatal hypoxia, [G. J. Zoppo et al., Drugs 54, 9 (1997); I. Sziraki et al., Neurosci. 85, 1101 (1998)].

SUMMARY

A salt compound having the formula (2) (below) is disclosed.

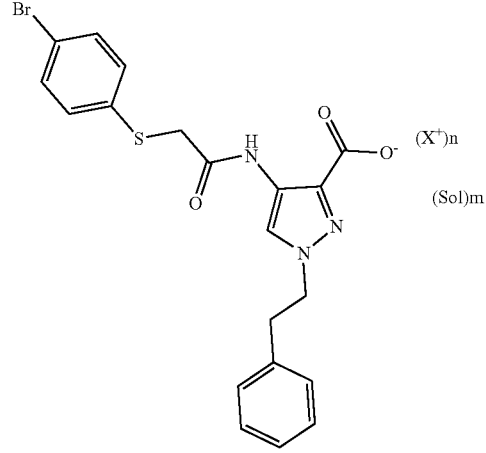

Formula 2

In a salt compound of the Formula 2:

n is 1, 2 or 3;

m is from 0 to 3 and can be a non-integer, m is typically 0, 0.5, 1, 2, or 3;

"Sol" is a solvent molecule and can be, for example, water or C2-C4 alcohol; and X+ is a cation, and can be, for example, a potassium ion, a sodium ion, a calcium ion, magnesium ion, ammonium ion or a substituted ammonium ion.

A salt compound of the Formula 2 can be prepared by treating the free base or zwitterion of Compound 1 (described below) with, for example, potassium hydroxide, sodium hydroxide, L-arginine, calcium hydroxide, N,N,N-trimethylglycine, ammonium hydroxide, magnesium hydroxide, choline, diethylamine, L-lysine, N,N'-dibenzylethylenediamine, M-ethylglucamine, calcium acetate, 1-(2-hydroxyethyl)pyrrolidine, N-(phenylmethyl)benzeneethaneamine, ammonia, magnesium acetate, N-methylglucamine, tromethamine, 4-(2-hydroxyethyl)morpholine, 2-(diethylamino)ethanol, or 2-dimethylaminoethanol.

BRIEF DESCRIPTION OF THE DRAWINGS

FIGS. 29A-29C show HSM analysis of sodium salt from a second preparation of KM-819. 29A—salt as prepared, 29B—at 136° C.—melt, 29C—re-crystallization.

FIG. 30 shows TGA analysis of sodium salt from a second preparation of KM-819.

DETAILED DESCRIPTION

Aminopyrazole derivatives are disclosed that inhibit ischemic cell death, and thus can be used as agents for preventing and treating ischemic diseases such as brain ischemia, heart ischemia, diabetic cardiovascular disease, heart failure, myocardial hypertrophy, retinal ischemia, ischemic colitis, ischemic acute renal failure, stroke, head trauma, Alzheimer's disease, Parkinson's disease, neonatal hypoxia, glaucoma and diabetic neuropathy, which are mediated by ischemic cell death, and as an agents for protecting organs during transplant procedures.

Compound 1 (KM-819) is a novel aminopyrazole derivative useful for the treatment of Parkinson's disease. The compound 1 (KM-819) disclosed can be synthesized as described by WO2008/051047 (hereby incorporated by reference in its entirety and for all purposes), providing a white, crystalline powder. Initial analysis of the compound 1 (KM-819), as the free acid or zwitterion, was performed to both understand more about the material and provide baseline data so that comparisons can be made between the compound 1 (KM-819) and any salts that are prepared.

One of ordinary skill in the art understands that the Compound 1 includes both a carboxylate group that can form an anion, and nitrogen centers that can form cationic quaternary amines. Thus, "Compound 1" can refer to either the free acid, or to zwitterionic forms of the compound, depending upon the pH of a solution of Compound 1.

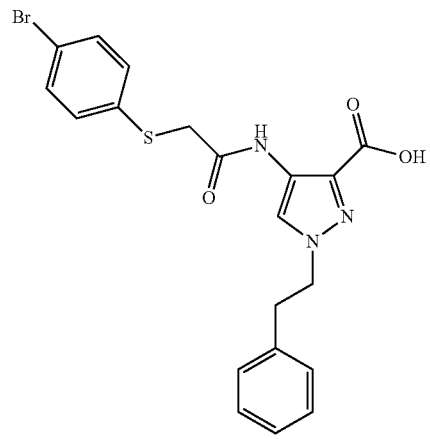

KM-819 (Compound 1)

Figure 1:
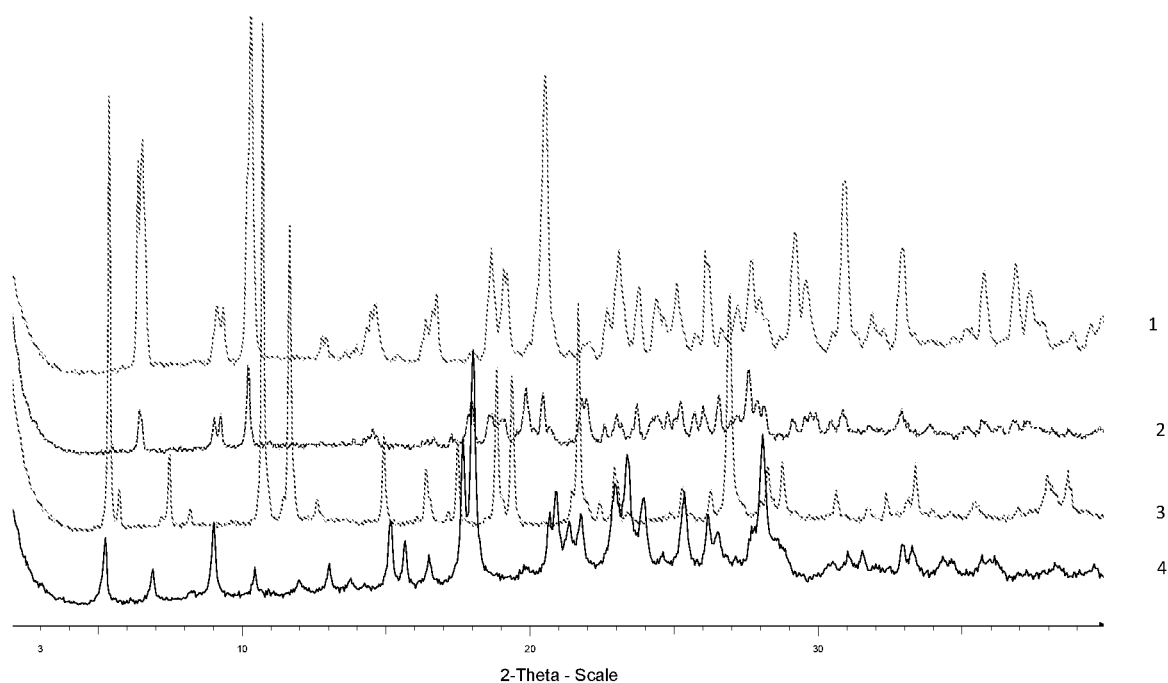
FIG. 1 shows XRPD diffraction of samples prepared with potassium hydroxide in different solvents. 1—from 4-methyl-pentan-2-one, 2—from diisopropyl ether, 3—from ethanol, 4—free acid.
Figure 2:
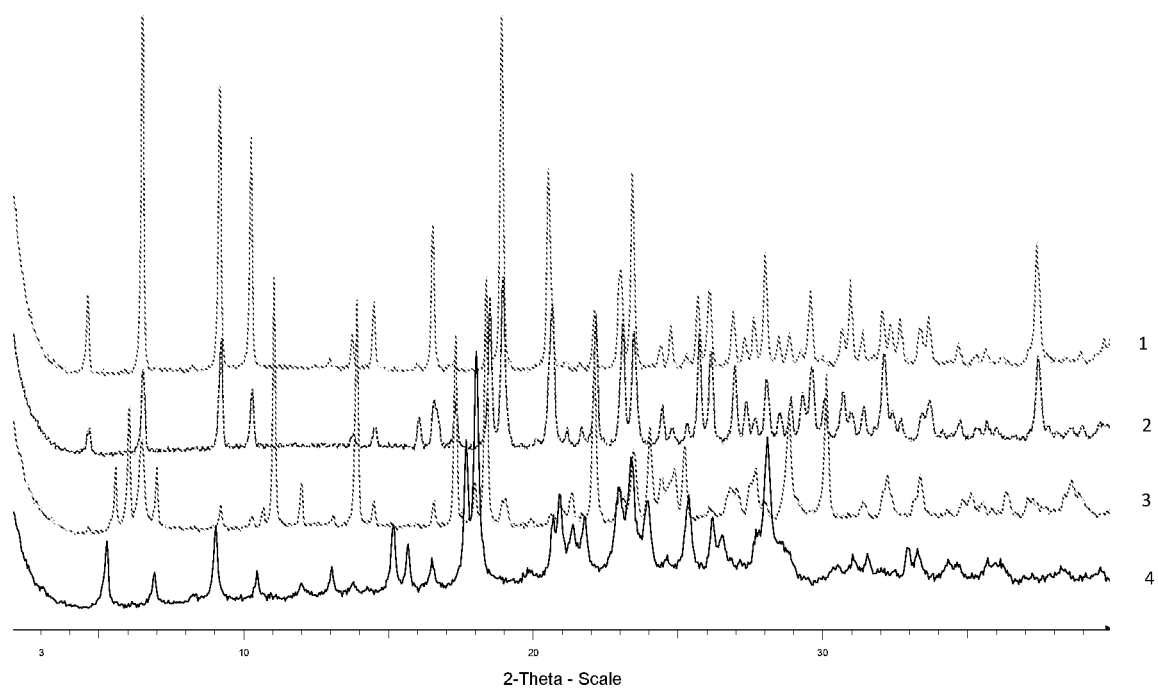
FIG. 2 shows XRPD diffraction of samples prepared with sodium hydroxide in different solvents. 1—from ethanol, 2—from diisopropyl ether, 3—from 4-methyl-pentan-2-one, 4—free acid.
Figure 3:
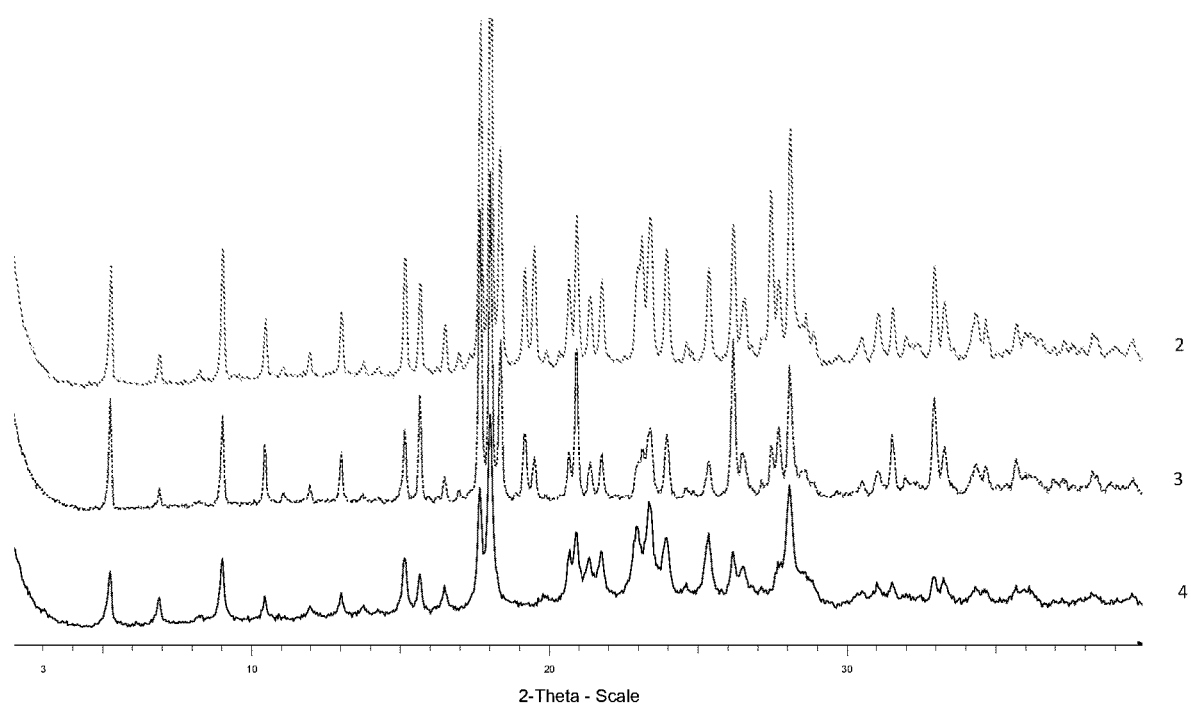
FIG. 3 shows XRPD diffraction of samples prepared with L-arginine in different solvents. 2—from diisopropyl ether, 3—from 4-methyl-pentan-2-one, 4—free acid.
Figure 4:
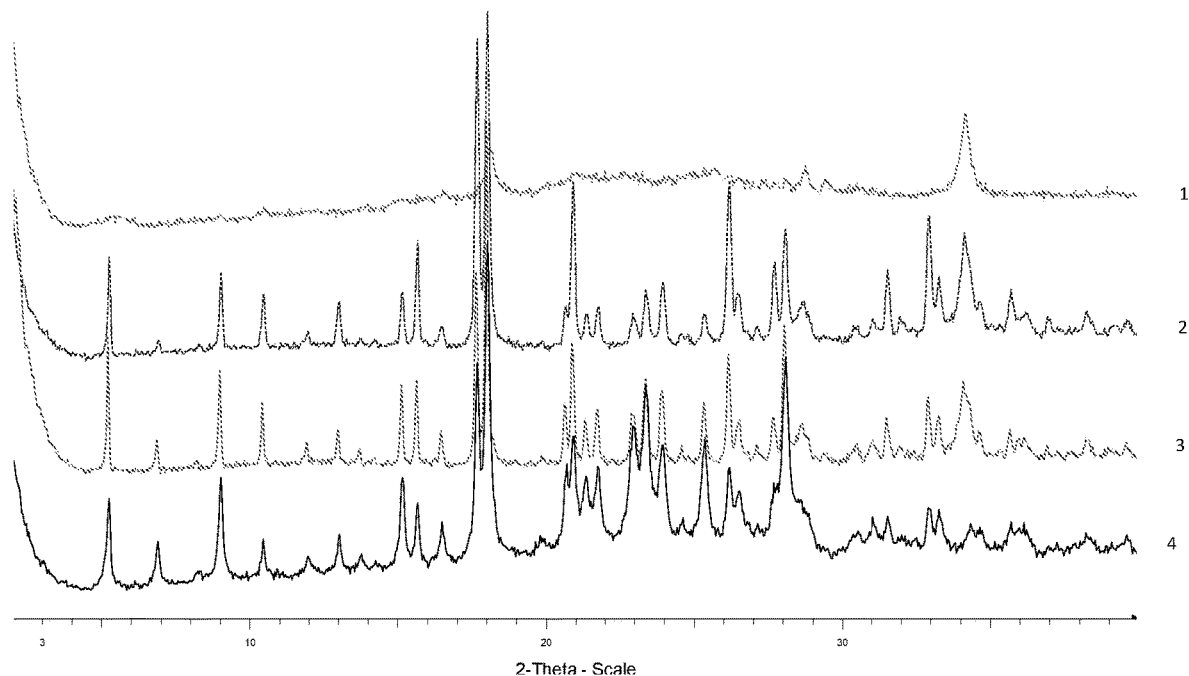
FIG. 4 shows XRPD diffraction of samples prepared with calcium hydroxide in different solvents. 1—from 4-methyl-pentan-2-one, 2—from diisopropyl ether, 3—ethanol, 4—free acid.
Figure 5:
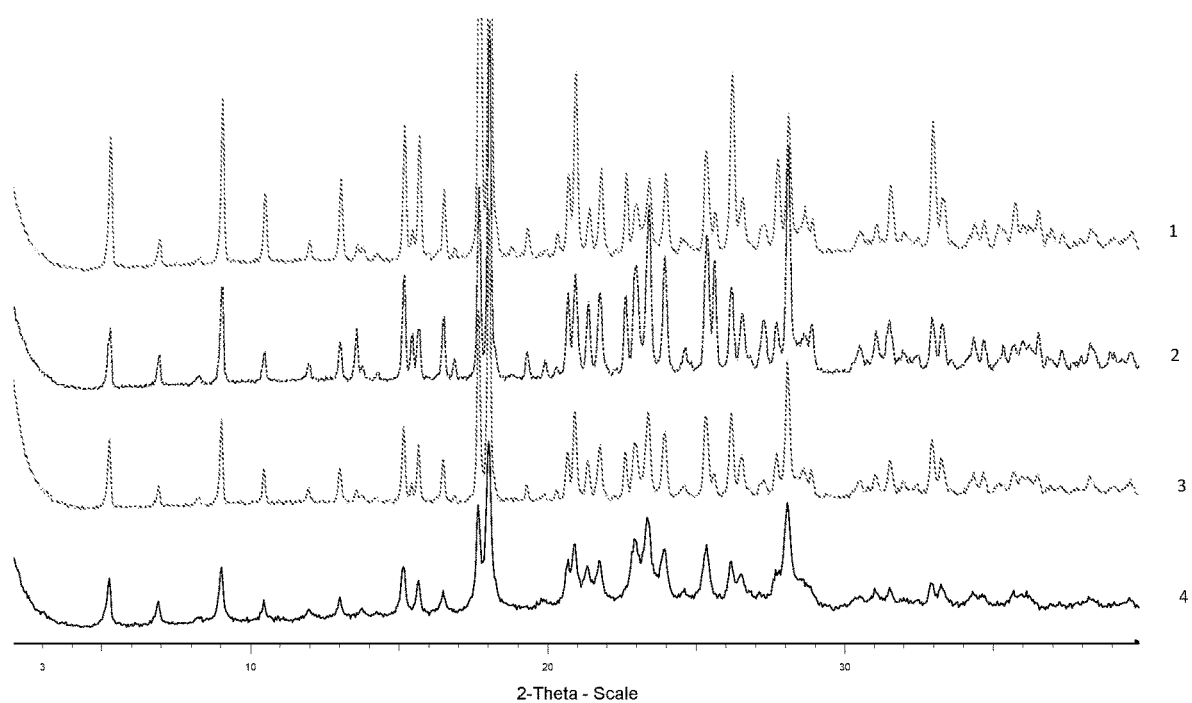
FIG. 5 shows XRPD diffraction of samples prepared with N,N,N-trimethylglycine indifferent solvents. 1—from 4-methyl-pentan-2-one, 2—from diisopropyl ether, 3—from ethanol, 4—free acid.
Figure 6:
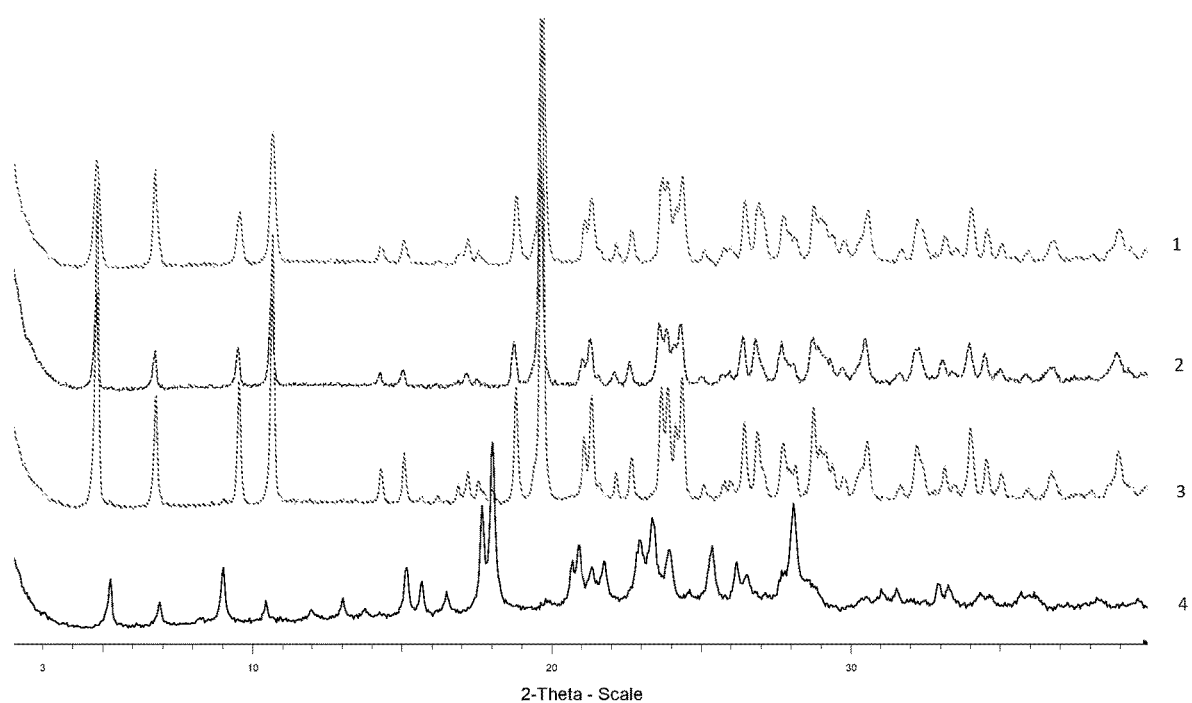
FIG. 6 shows XRPD diffraction of samples prepared with ammonium hydroxide in different solvents. 1—from 4-methyl-pentan-2-one, 2—from diisopropyl ether, 3—from ethanol, 4—free acid.
Figure 7:
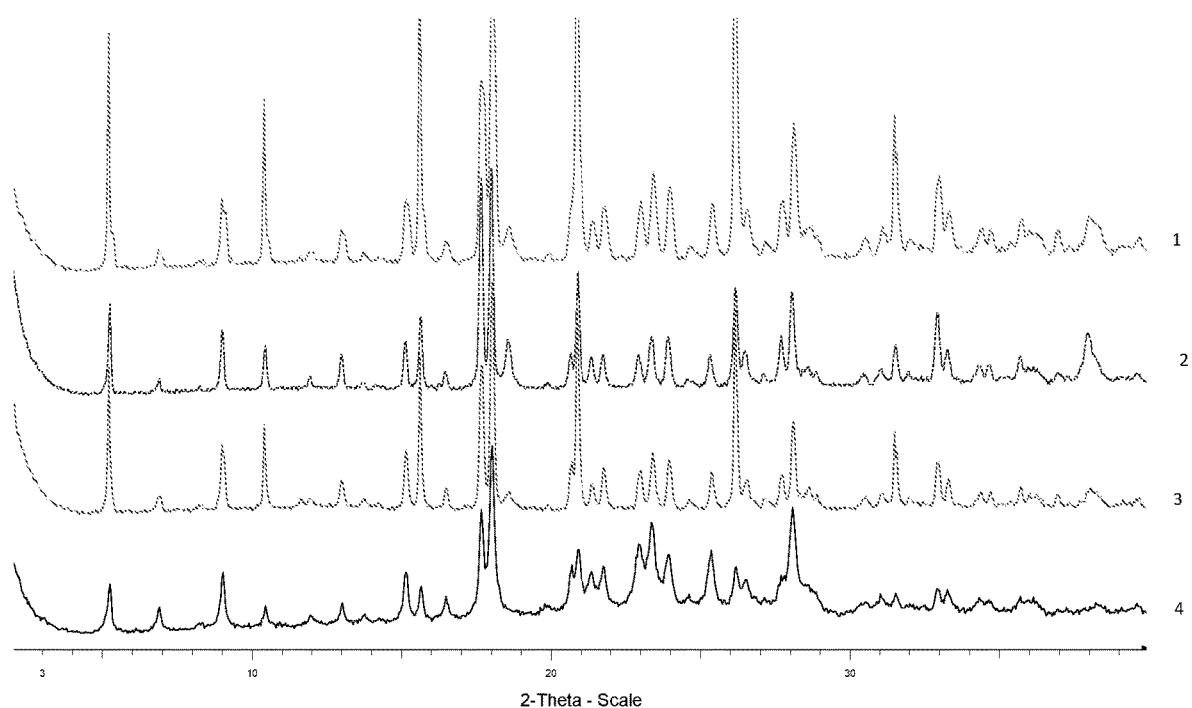
FIG. 7 shows XRPD diffraction of samples prepared with magnesium hydroxide in different solvents. 1—from 4-methyl-pentan-2-one, 2—from diisopropyl ether, 3—from ethanol, 4—free acid.
Figure 8:
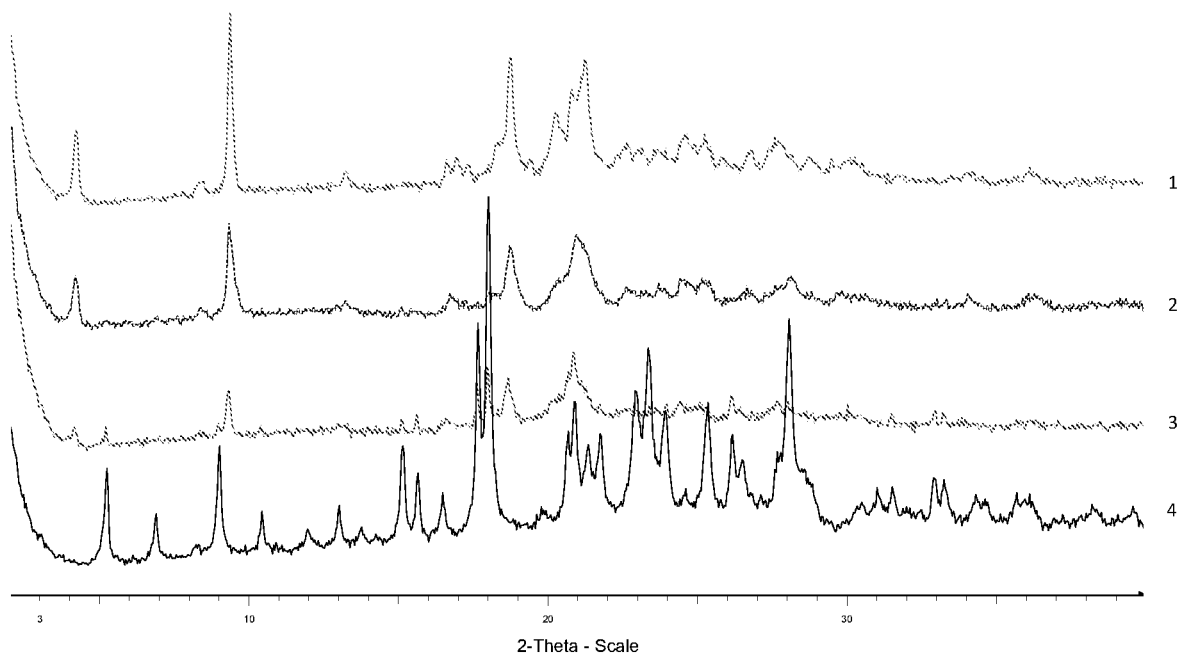
FIG. 8 shows XRPD diffraction of samples prepared with choline in different solvents. 1—from 4-methyl-pentan-2-one, 2—from diisopropyl ether, 3—from ethanol, 4—free acid.
Figure 9:
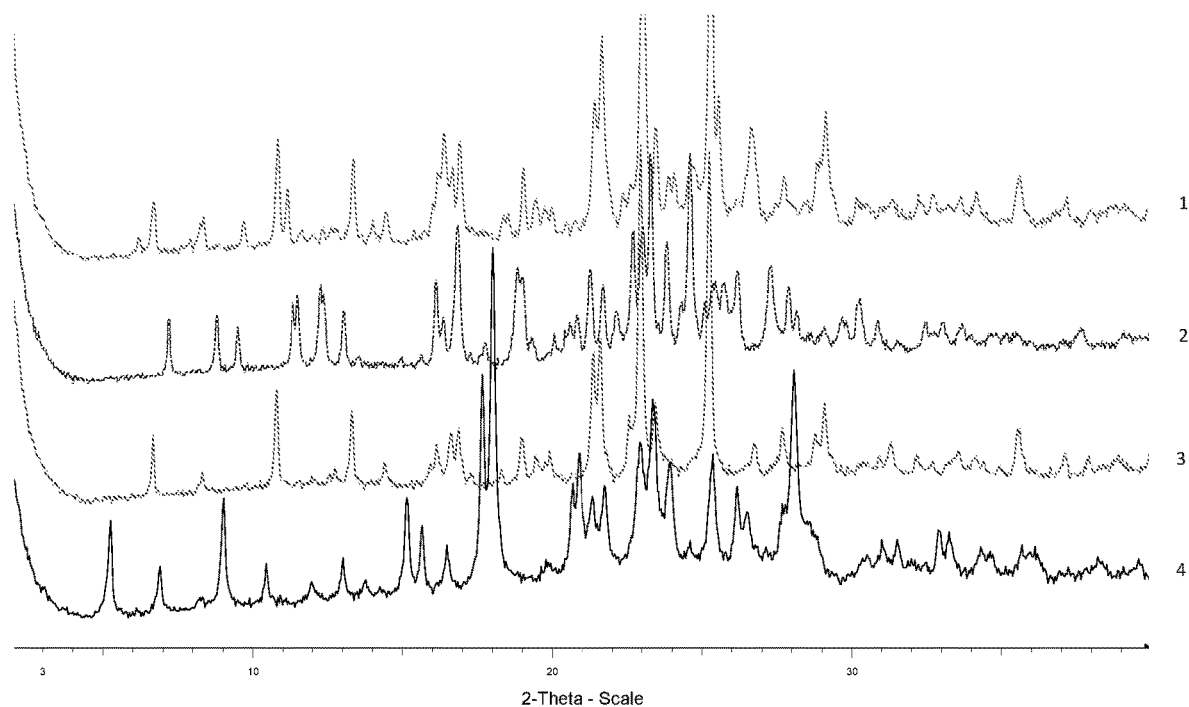
FIG. 9 shows XRPD diffraction of samples prepared with diethylamine in different solvents. 1—from 4-methyl-pentan-2-one, 2—from diisopropyl ether, 3—from ethanol, 4—free acid.
Figure 10:
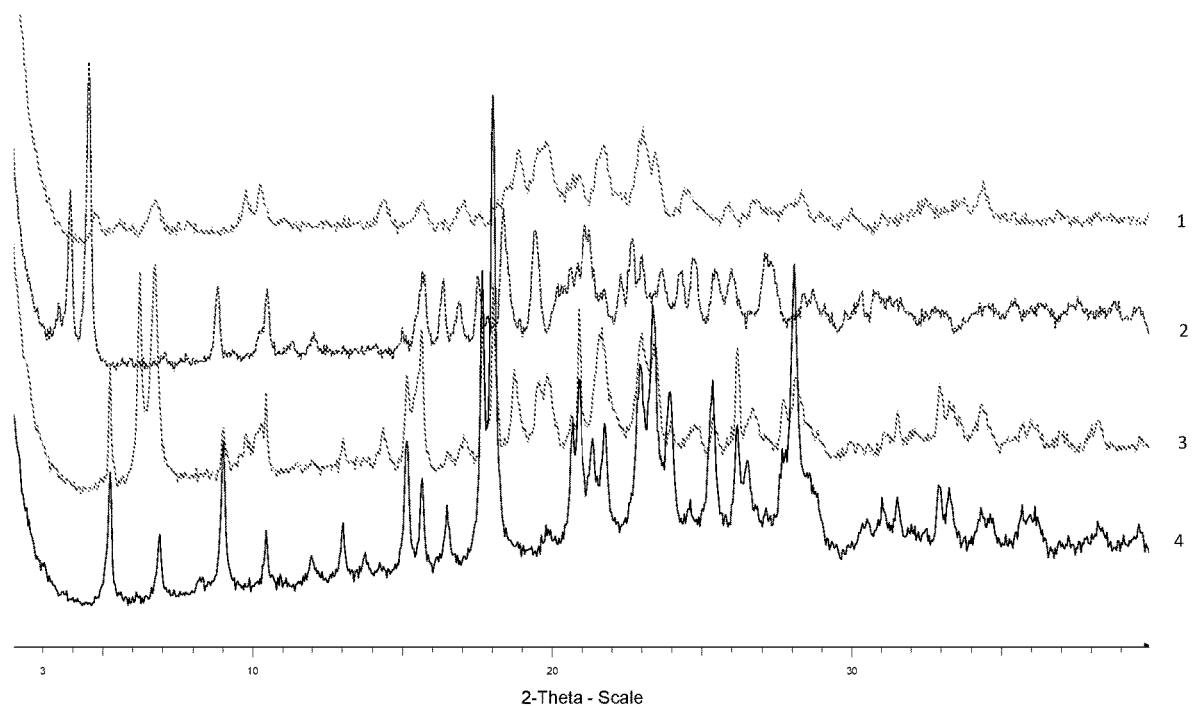
FIG. 10 shows XRPD diffraction of samples prepared with L-lysine in different solvents. 1—from 4-methyl-pentan-2-one, 2—from diisopropyl ether, 3—from ethanol, 4—free acid.
Figure 11:
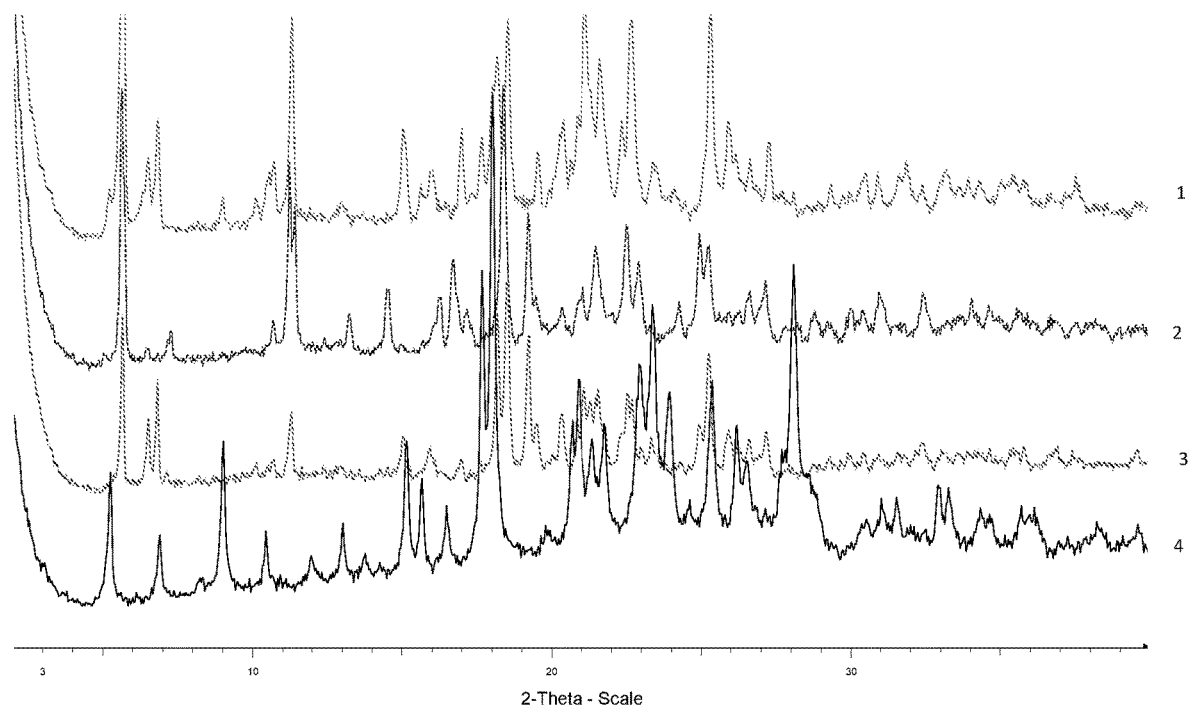
FIG. 11 shows XRPD diffraction of samples prepared with N,N'-dibenzylethylenediamine in different solvents. 1—from 4-methyl-pentan-2-one, 2—from diisopropyl ether, 3—from ethanol, 4—free acid.
Figure 12:
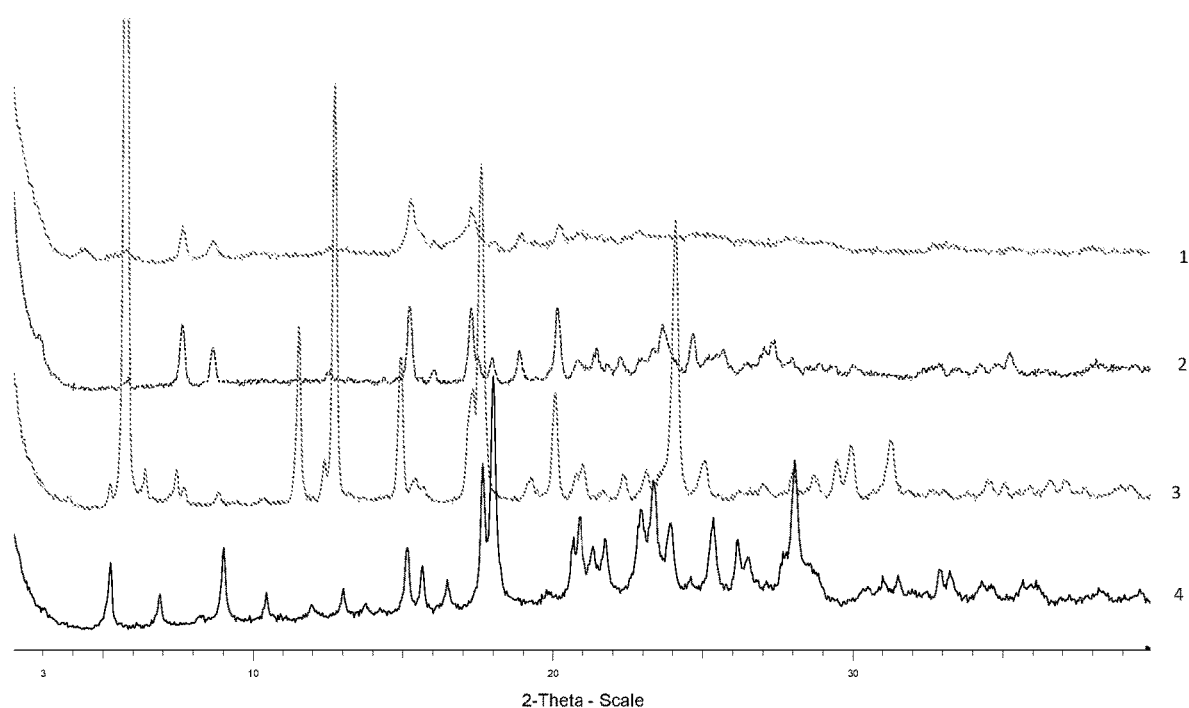
FIG. 12 shows XRPD diffraction of samples prepared with N-ethylglucamine in different solvents. 1—from 4-methyl-pentan-2-one, 2—from diisopropyl ether, 3—from ethanol, 4—free acid.
Figure 13:
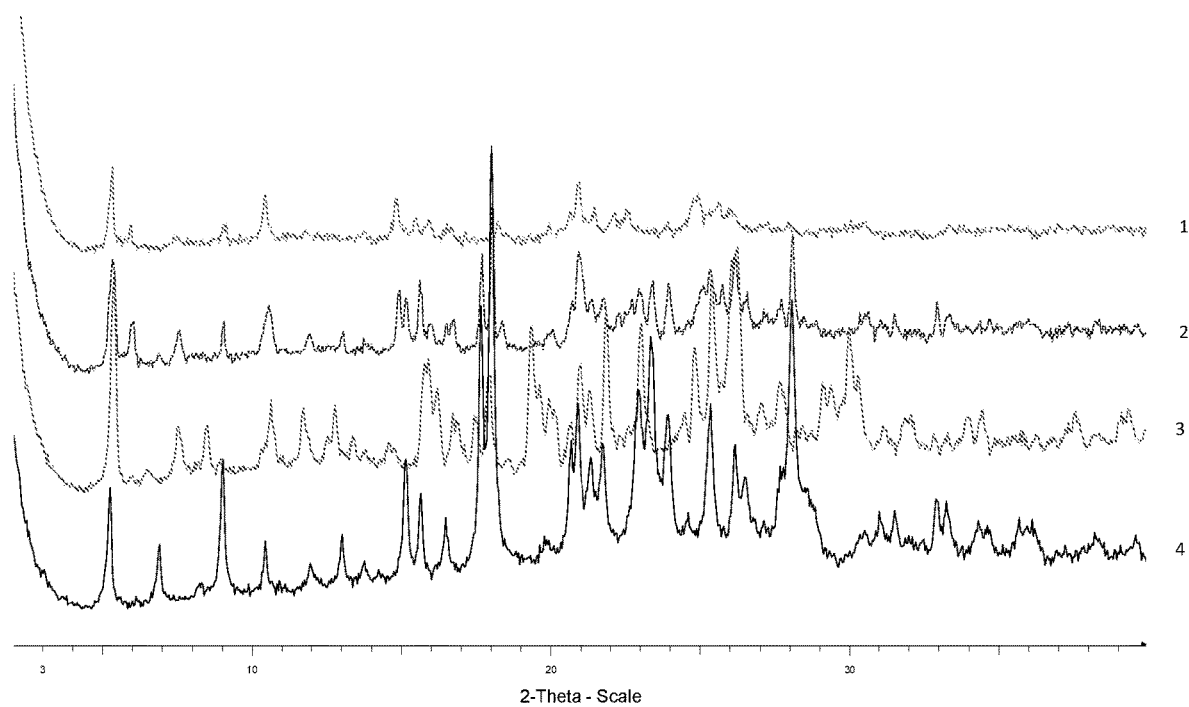
FIG. 13 shows XRPD diffraction of samples prepared with calcium acetate in different solvents. 1—from 4-methyl-pentan-2-one, 2—from diisopropyl ether, 3—from ethanol, 4—free acid.
Figure 14:
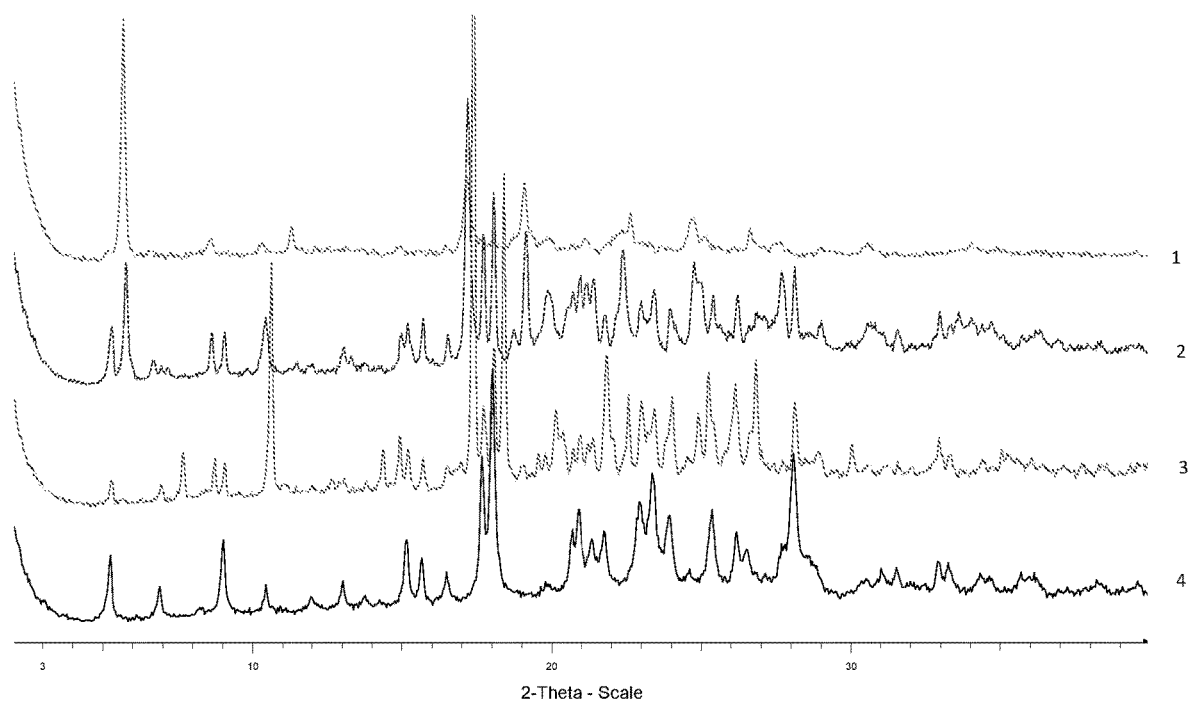
FIG. 14 shows XRPD diffraction of samples prepared with N-(phenylmethyl) benzeneethaneamine in different solvents. 1—from 4-methyl-pentan-2-one, 2—from diisopropyl ether, 3—from ethanol, 4—free acid.
Figure 15:
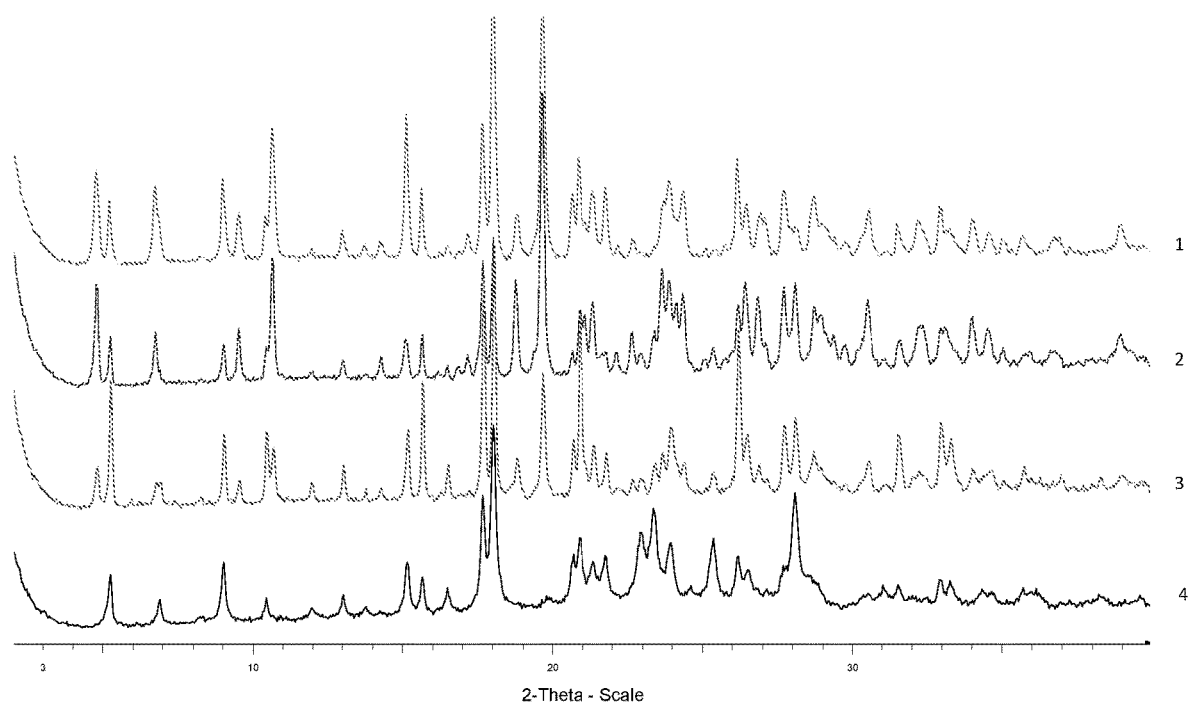
FIG. 15 shows XRPD diffraction of samples prepared with ammonia in different solvents. 1—from 4-methyl-pentan-2-one, 2—from diisopropyl ether, 3—from ethanol, 4—free acid.
Figure 16:
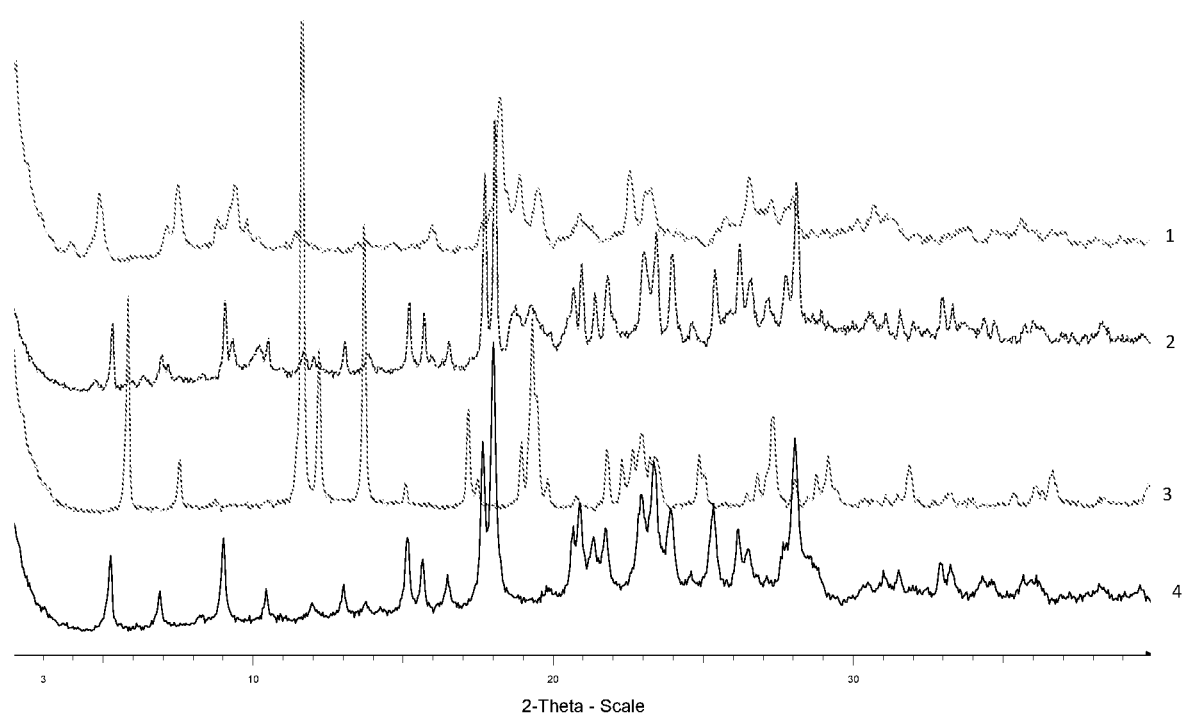
FIG. 16 shows XRPD diffraction of samples prepared with magnesium acetate in different solvents. 1—from 4-methyl-pentan-2-one, 2—from diisopropyl ether, 3—from ethanol, 4—free acid.
Figure 17:
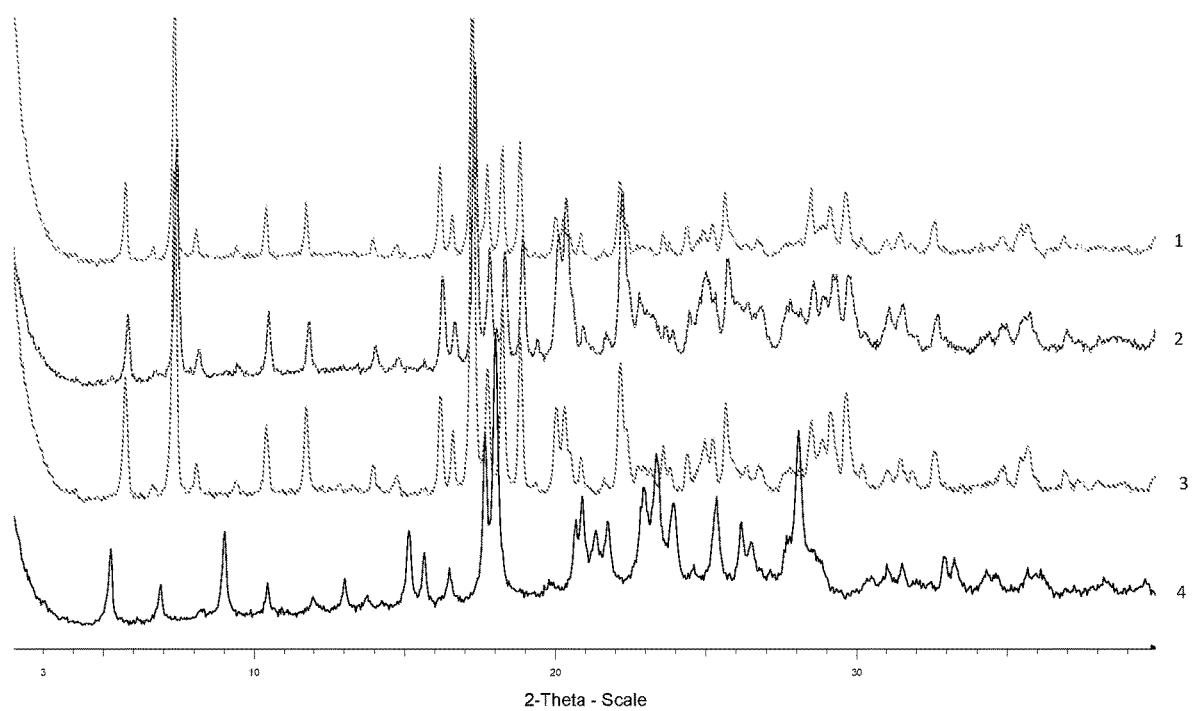
FIG. 17 shows XRPD diffraction of samples prepared with N-methylglucamine in different solvents. 1—from 4-methyl-pentan-2-one, 2—from diisopropyl ether, 3—from ethanol, 4—free acid.
Figure 18:
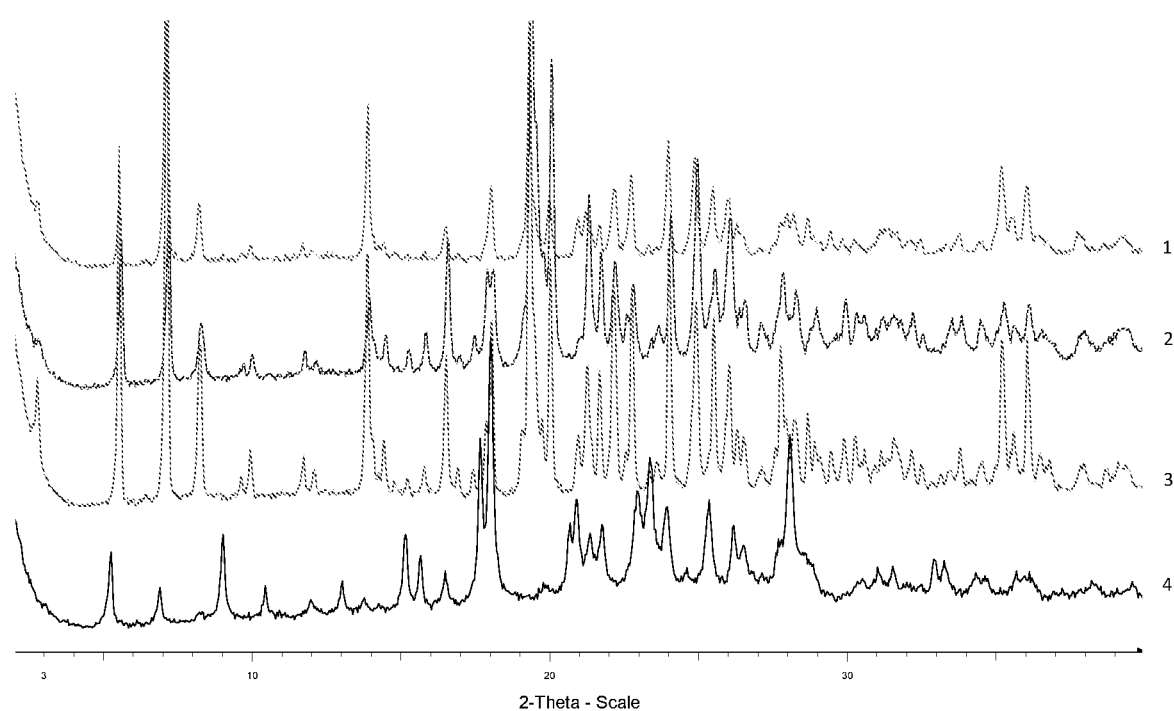
FIG. 18 shows XRPD diffraction of samples prepared with tromethamine in different solvents. 1—from 4-methyl-pentan-2-one, 2—from diisopropyl ether, 3—from ethanol, 4—free acid.
Figure 19:
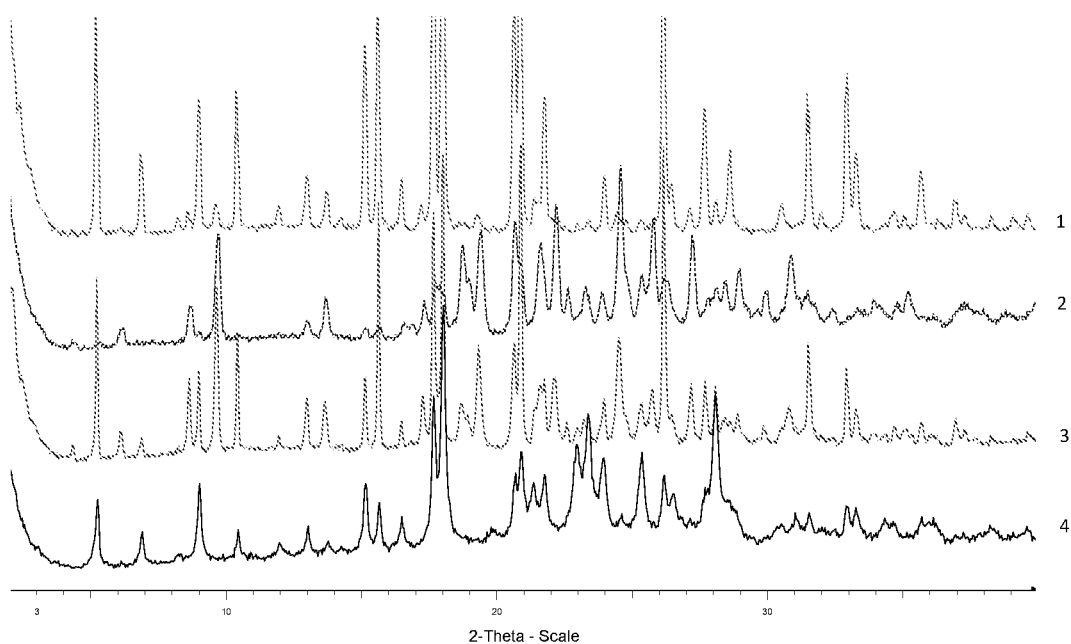
FIG. 19 shows XRPD diffraction of samples prepared with 4-(2-hydroxyethyl)morpholine in different solvents. 1—from 4-methyl-pentan-2-one, 2—from diisopropyl ether, 3—from ethanol, 4—free acid.
Figure 20:
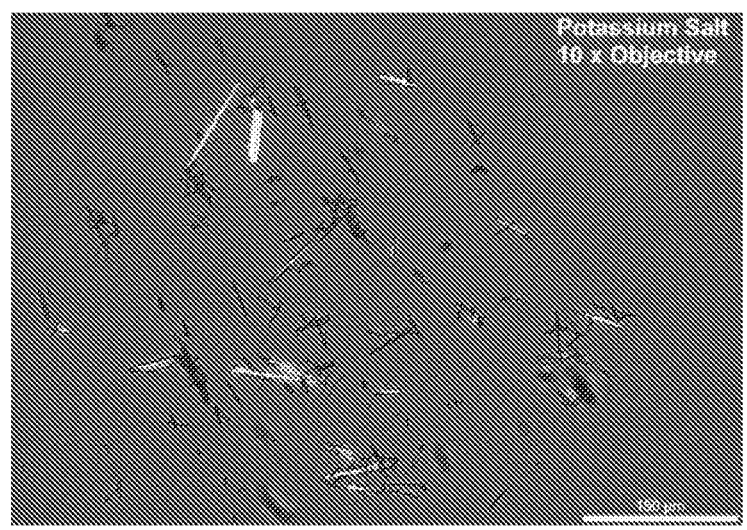
FIG. 20 shows PLM analysis of potassium salt Formula 2 from a second preparation of KM-819.
Figure 21:
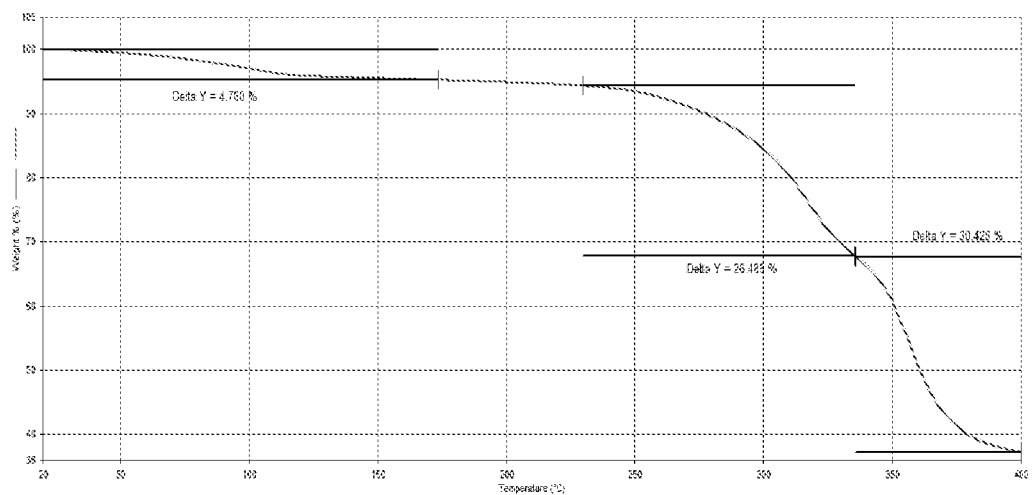
FIG. 21 shows TGA analysis of Potassium salt Formula 2 from a second preparation of KM-819.
Figure 22:
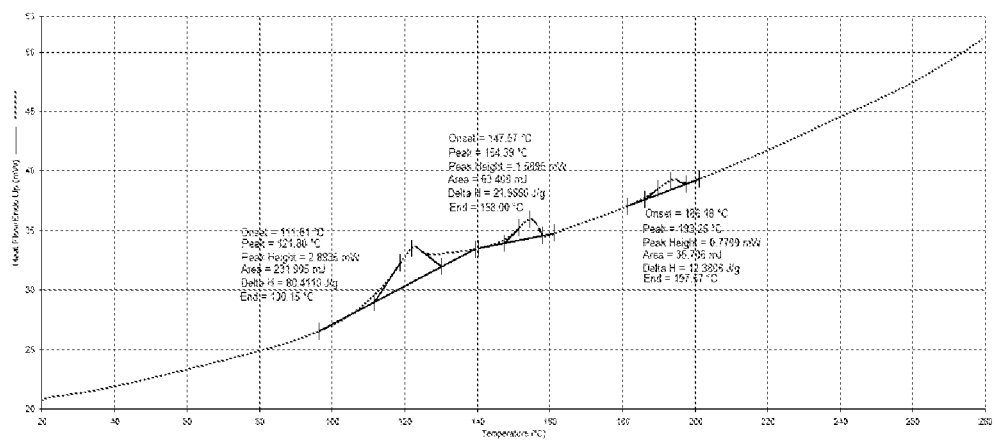
FIG. 22 shows Differential Scanning calorimetery (DSC) analysis of potassium salt Formula 2 from a second preparation of KM-819.
Figure 23A:
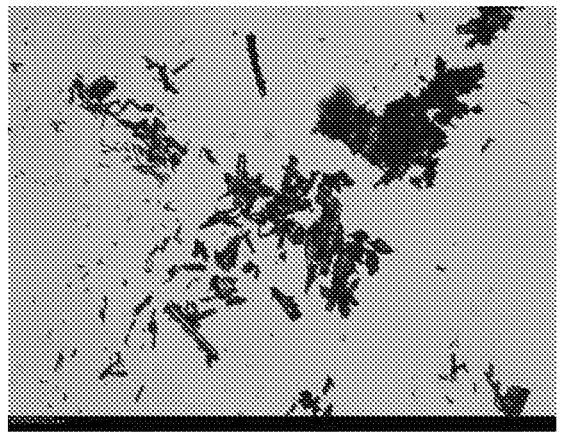
FIGS. 23A-23E shows HSM analysis of potassium salt Formula 2 from a second preparation of KM-819. 23A: potassium salt initial condition, 23B: 127° C.—loss of birefringence, 23C: 154° C.—initial melt, 23D: 212° C.—secondary melt, 23E: re-crystallisation.
Figure 23B:
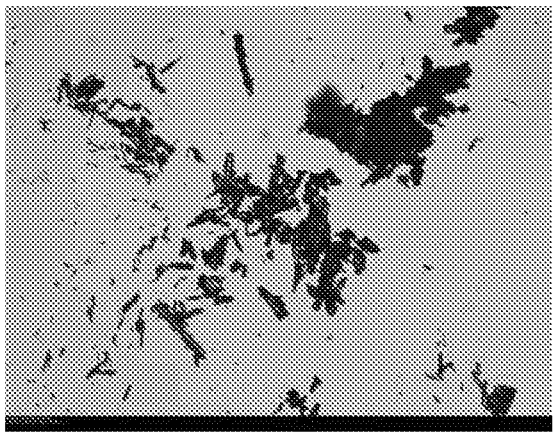
Figure 23C:
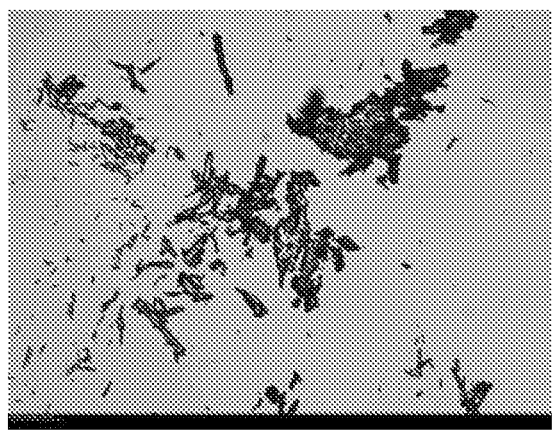
Figure 23D:
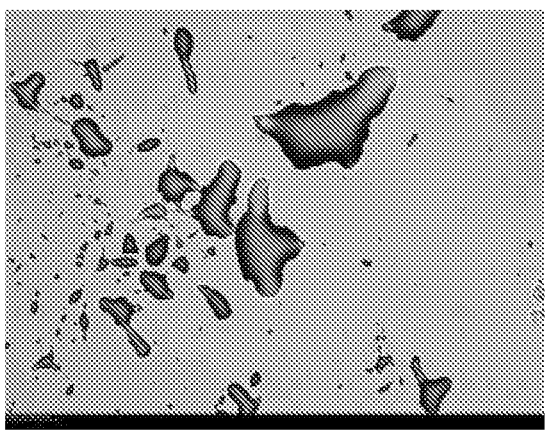
Figure 23E:
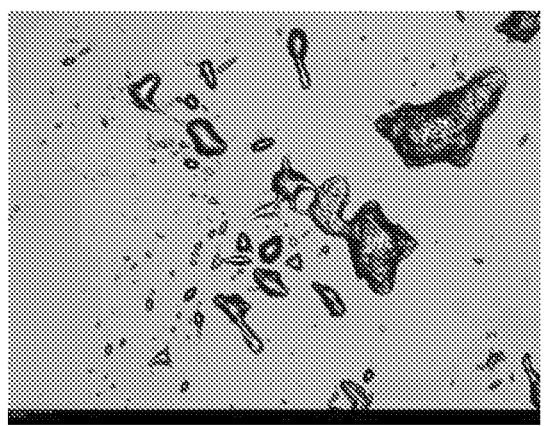
Figure 24:
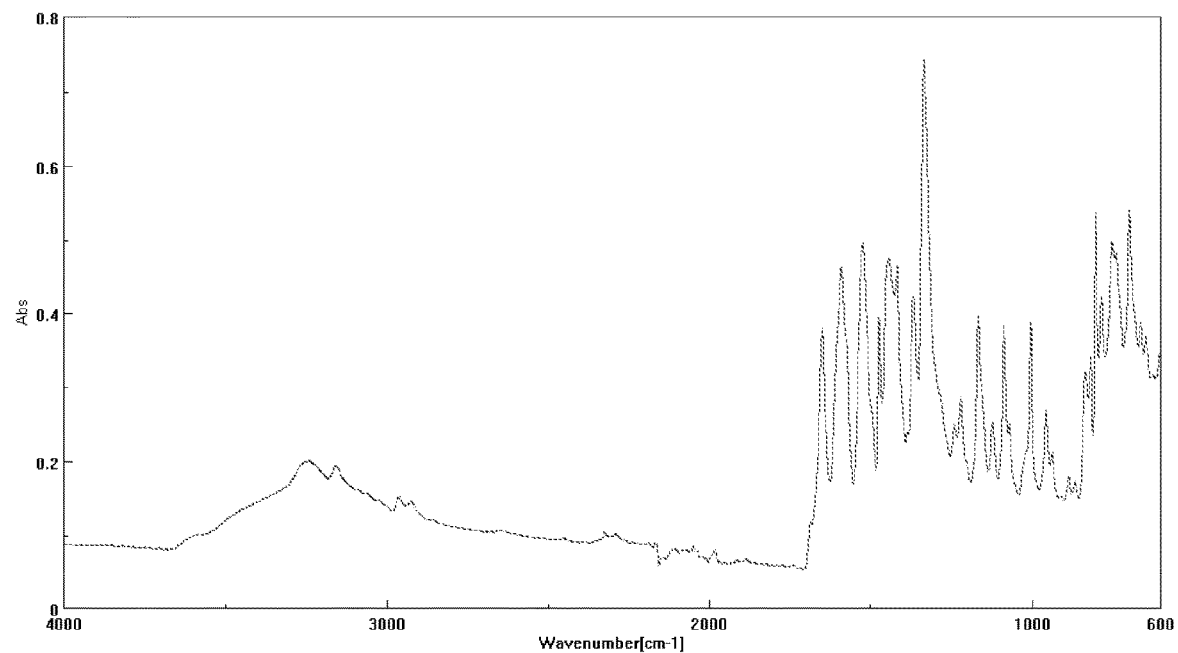
FIG. 24 shows Fourier Transform Infra-Red (FT-IR) analysis of potassium salt Formula 2 from a second preparation of KM-819.
Figure 25:
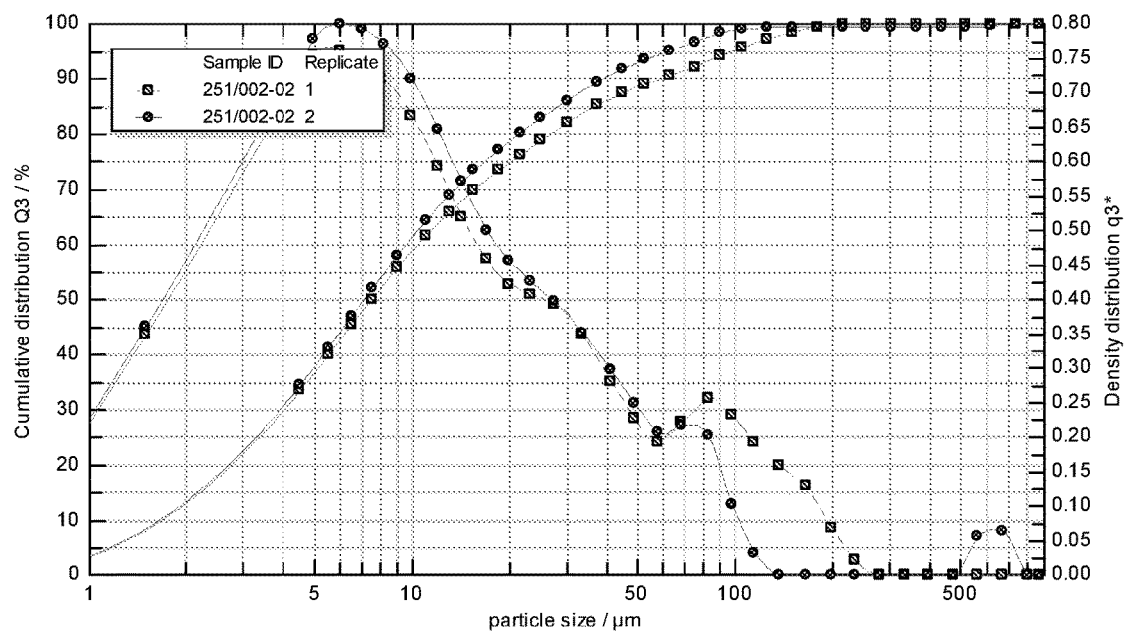
FIG. 25 shows Particle Size Distribution (PSD) of potassium salt Formula 2 from a second preparation of KM-819.
Figure 26:
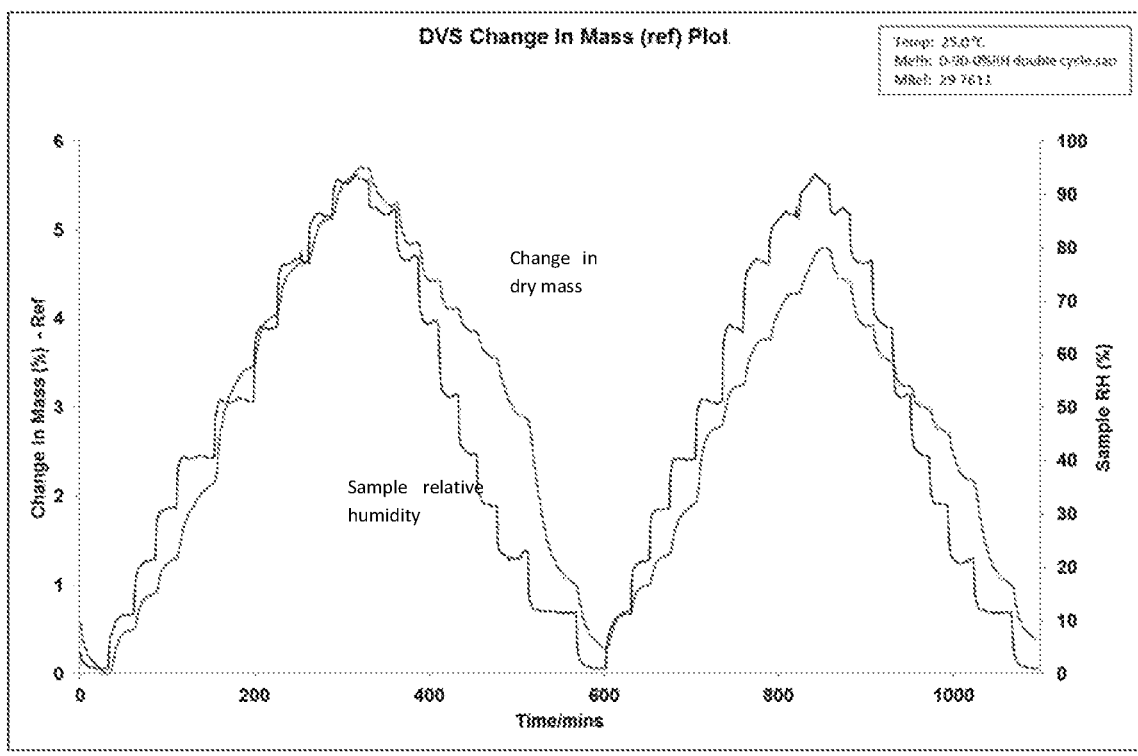
FIG. 26 shows a DVS change in mass plot of potassium salt Formula 2 from a second preparation of KM-819.
Figure 27:
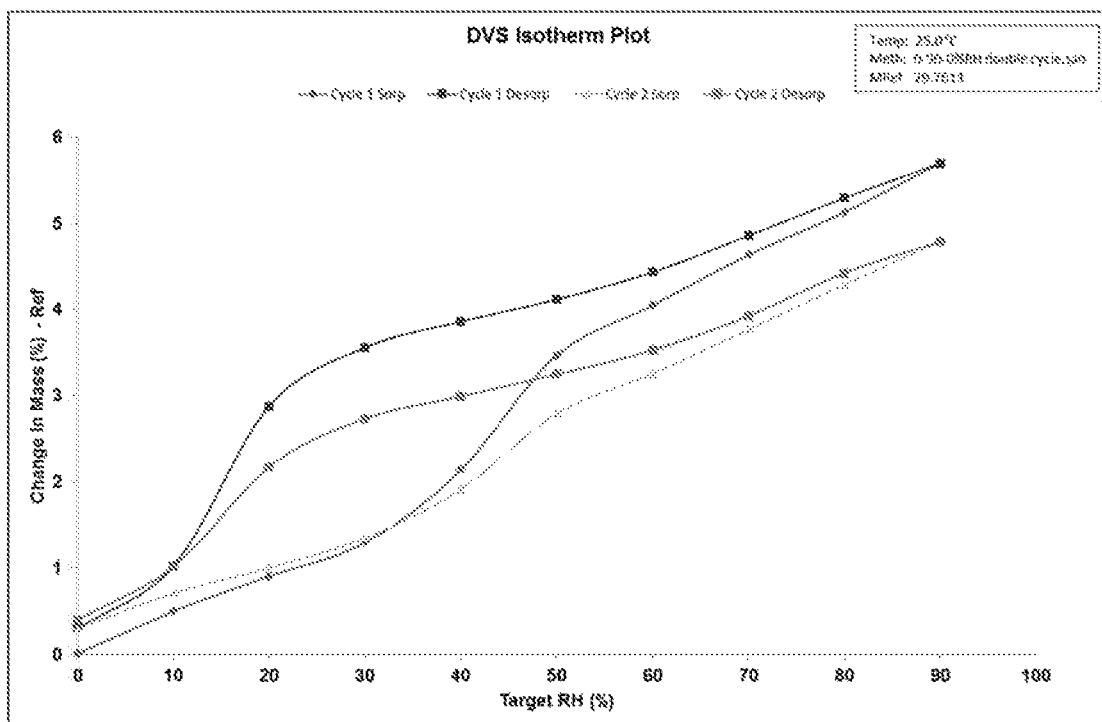
FIG. 27 shows a DVS isotherm plot of potassium salt Formula 2 from a second preparation of KM-819.
Figure 28:
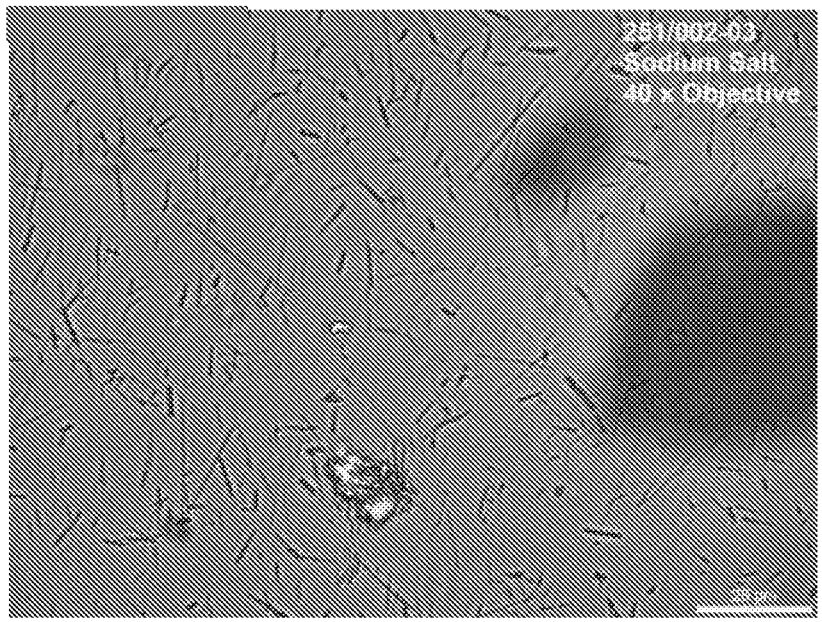
FIG. 28 shows PLM analysis of sodium salt from a second preparation of KM-819.
Figure 31:
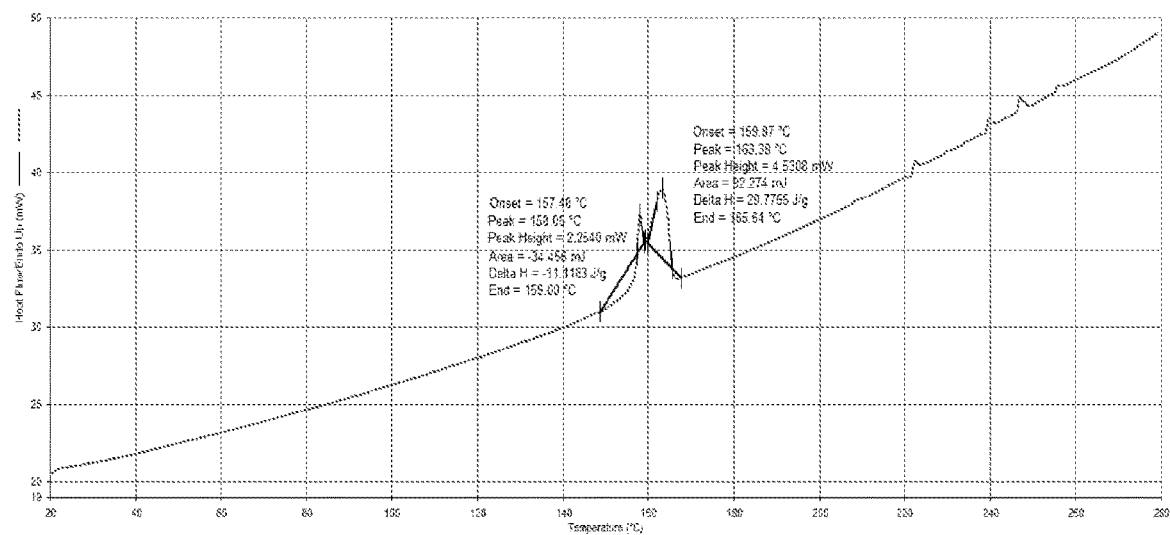
FIG. 31 shows DSC analysis of sodium salt from a second preparation of KM-819.
Figure 32:
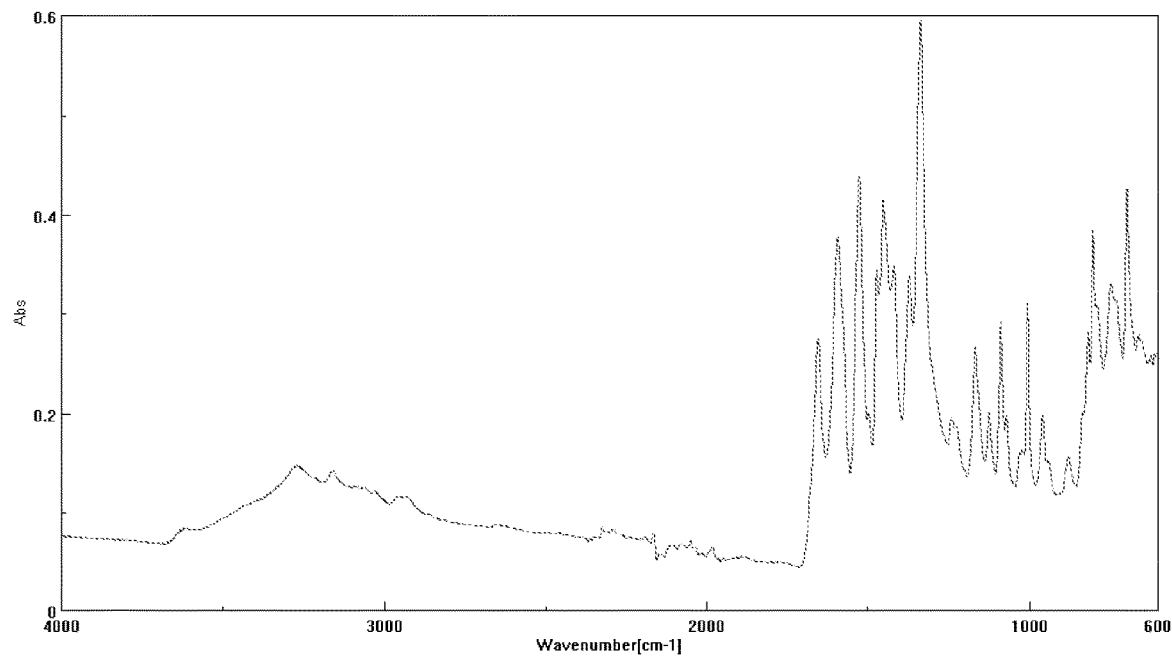
FIG. 32 shows FT-IR analysis of sodium salt from a second preparation of KM-819.
Figure 33:
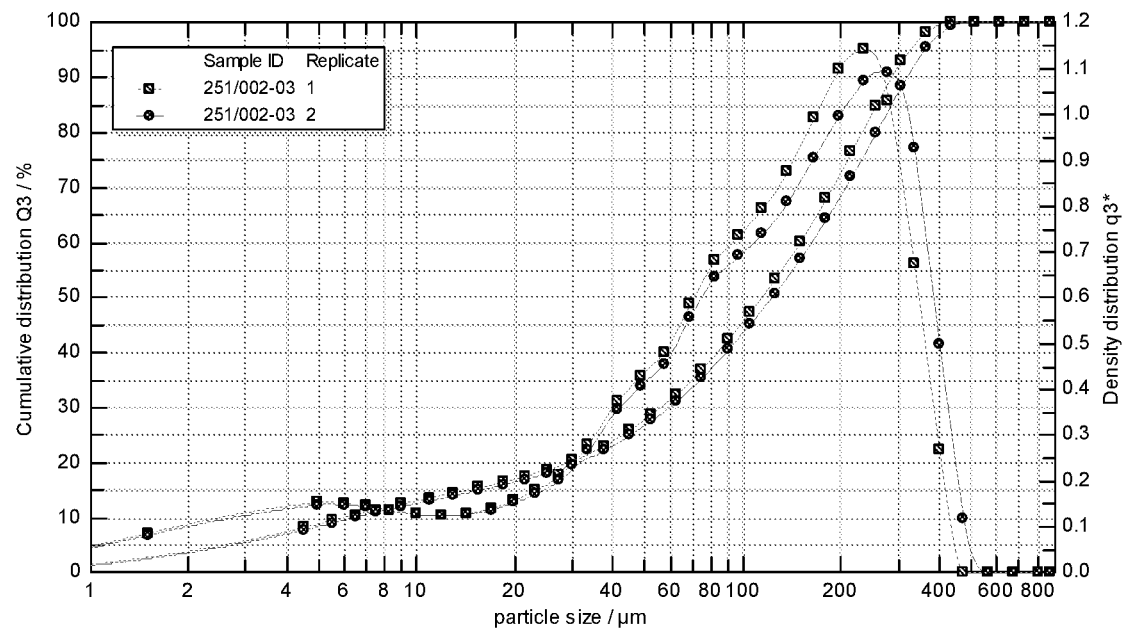
FIG. 33 shows Sympatec PSD analysis of sodium salt from a second preparation of KM-819.
Figure 34:
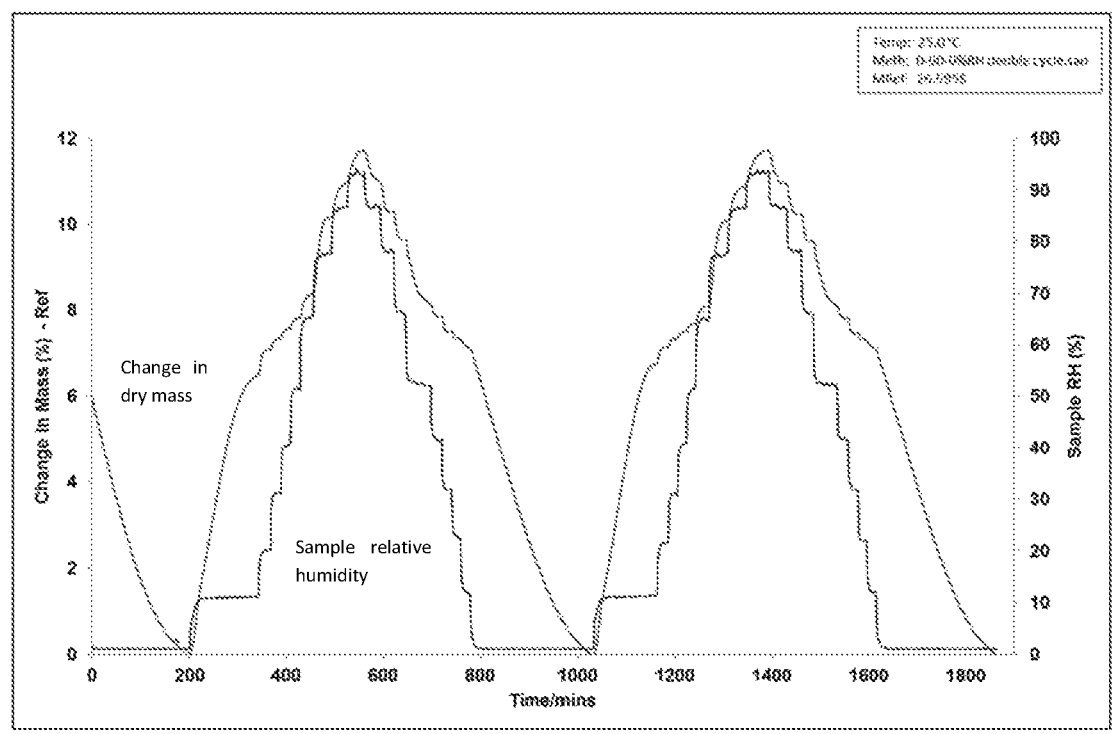
FIG. 34 shows a DVS change in mass plot of a sodium salt from a second preparation of KM-819.
Figure 35:
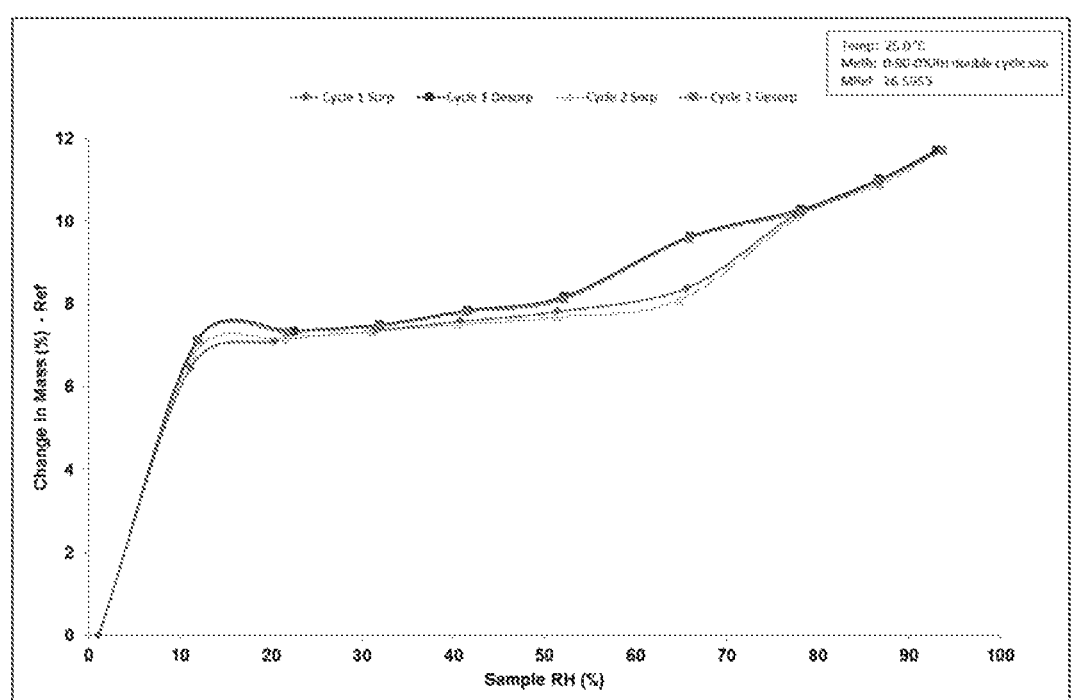
FIG. 35 shows a DVS isotherm plot of sodium salt from a second preparation of KM-819.
Figure 36:
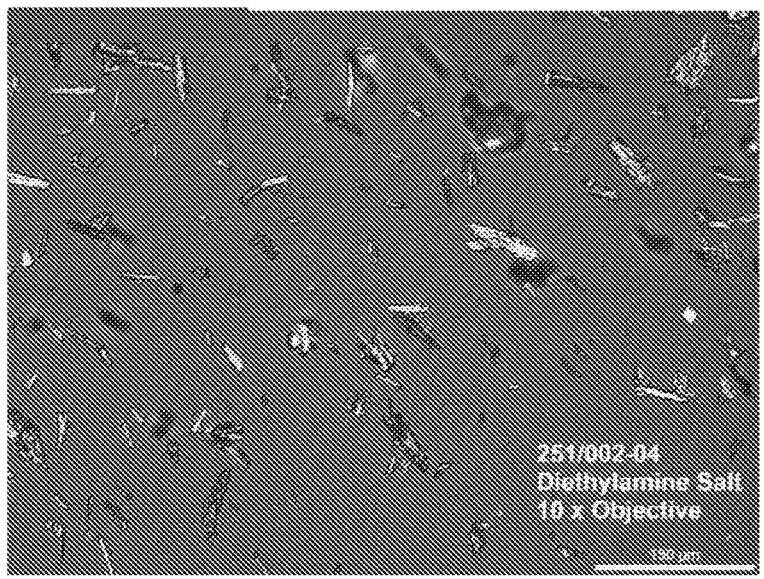
FIG. 36 shows PLM analysis of a diethylamine salt Formula 2 from a second preparation of KM-819.
Figure 37:
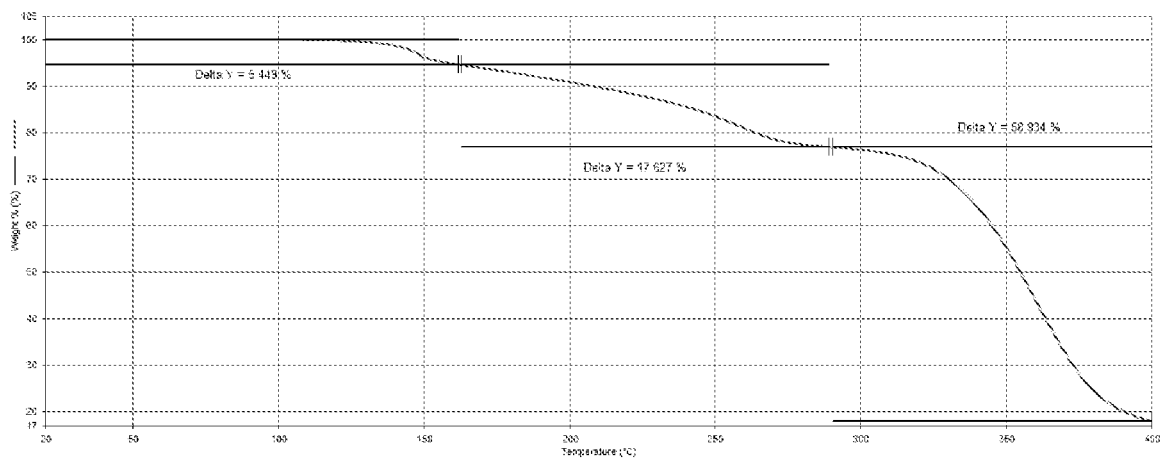
FIG. 37 shows TGA analysis of a diethylamine salt Formula 2 from a second preparation of KM-819.
Figure 38:
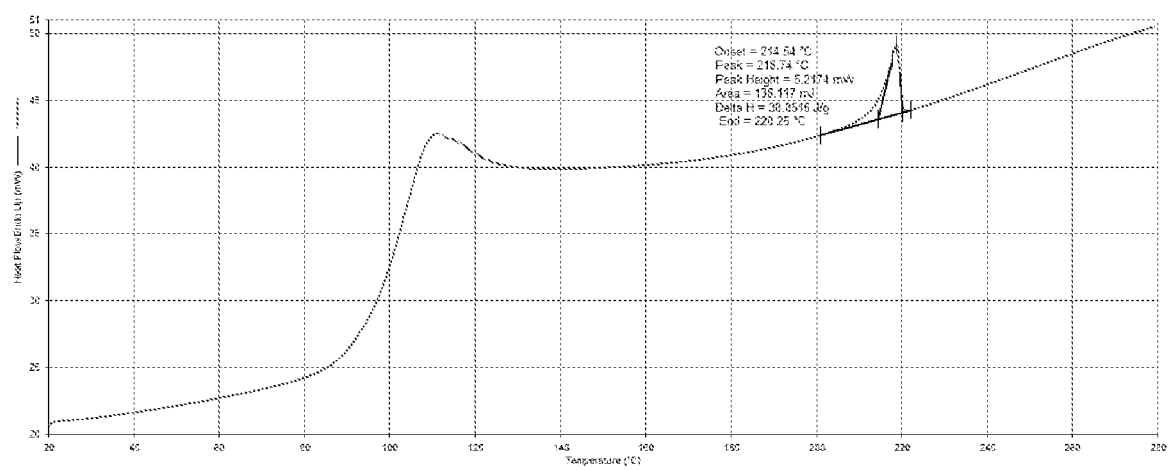
FIG. 38 shows DSC analysis of a diethylamine salt Formula 2 from a second preparation of KM-819.
Figure 39A:
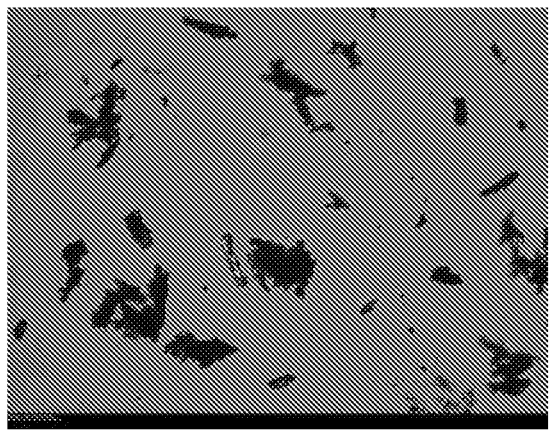
FIGS. 39A-E show HSM analysis of a diethylamine salt Formula 2 from a second preparation of KM-819. 39A—diethylamine salt as prepared, 39B—at 154° C.—initial melt, 39C—at 200° C.—particle movement, 39D—at 209° C.—secondary melt, 39E—re-crystallization.
Figure 39B:
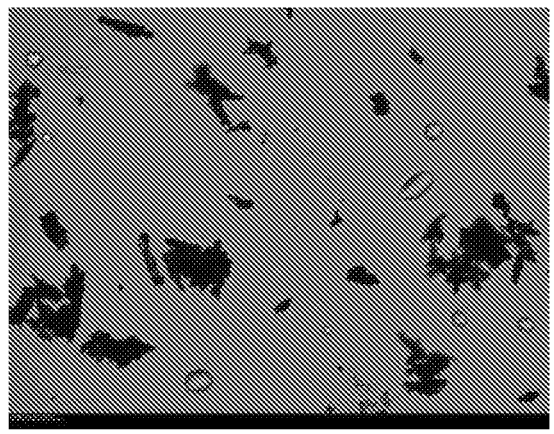
Figure 39C:
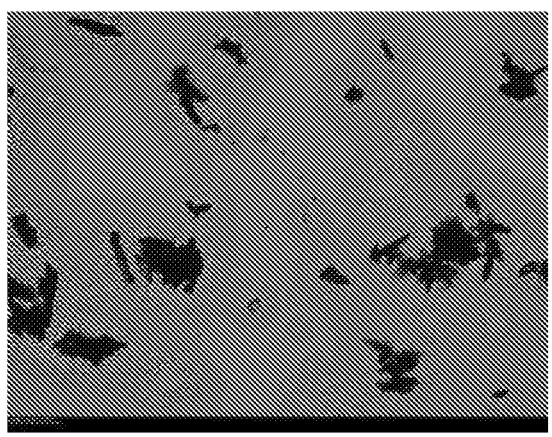
Figure 39D:
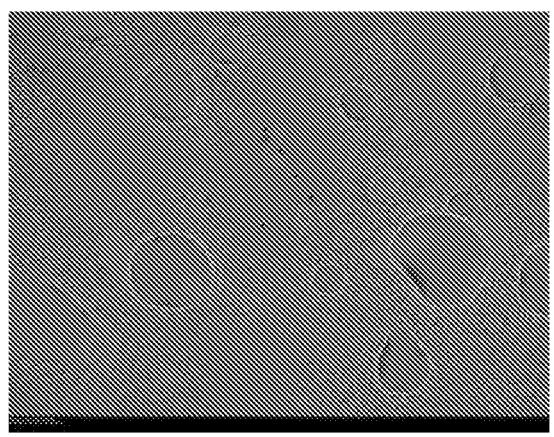
Figure 39E:
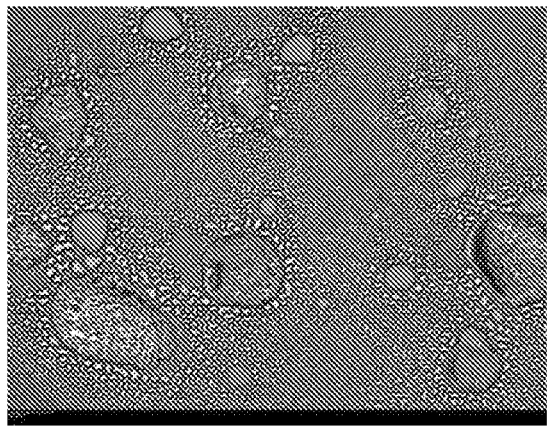
Figure 40:
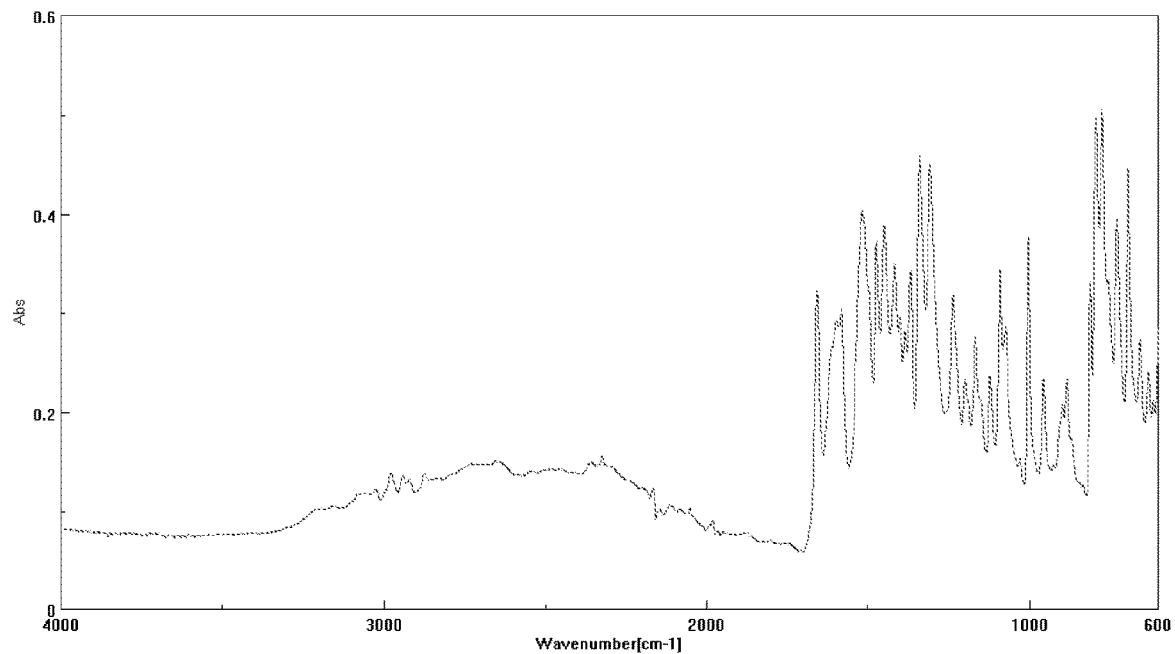
FIG. 40 shows FT-IR analysis of a diethylamine salt Formula 2 from a second preparation of KM-819.
Figure 41:
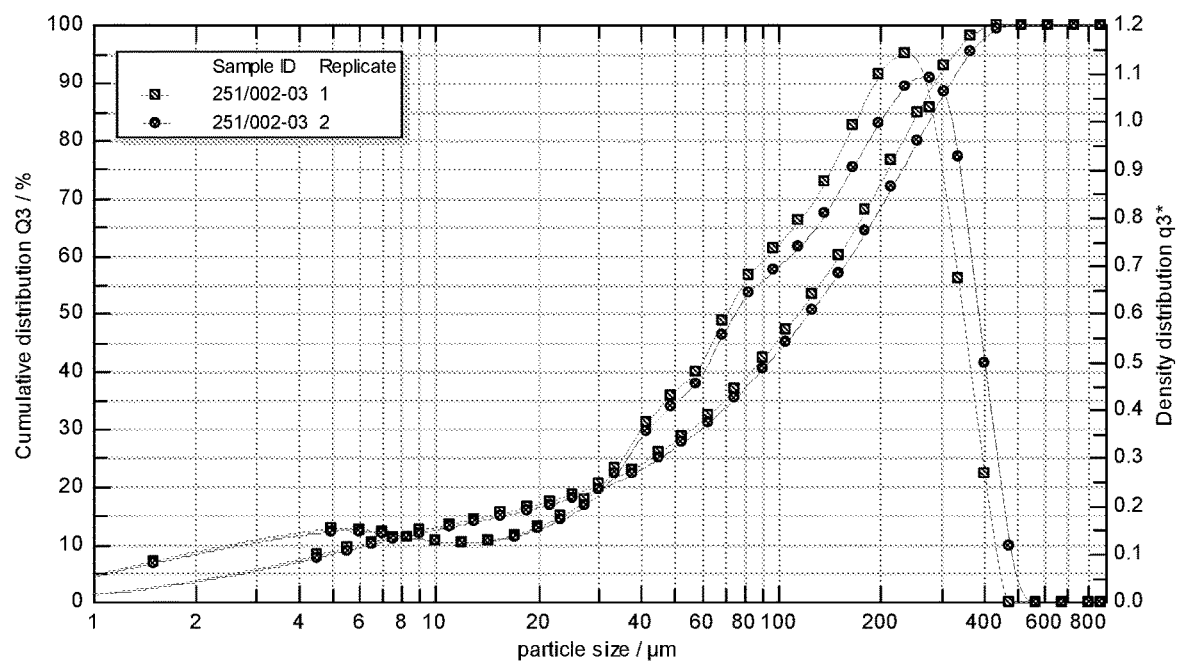
FIG. 41 shows Sympatec PSD of a diethylamine salt Formula 2 from a second preparation of KM-819.
Figure 42:
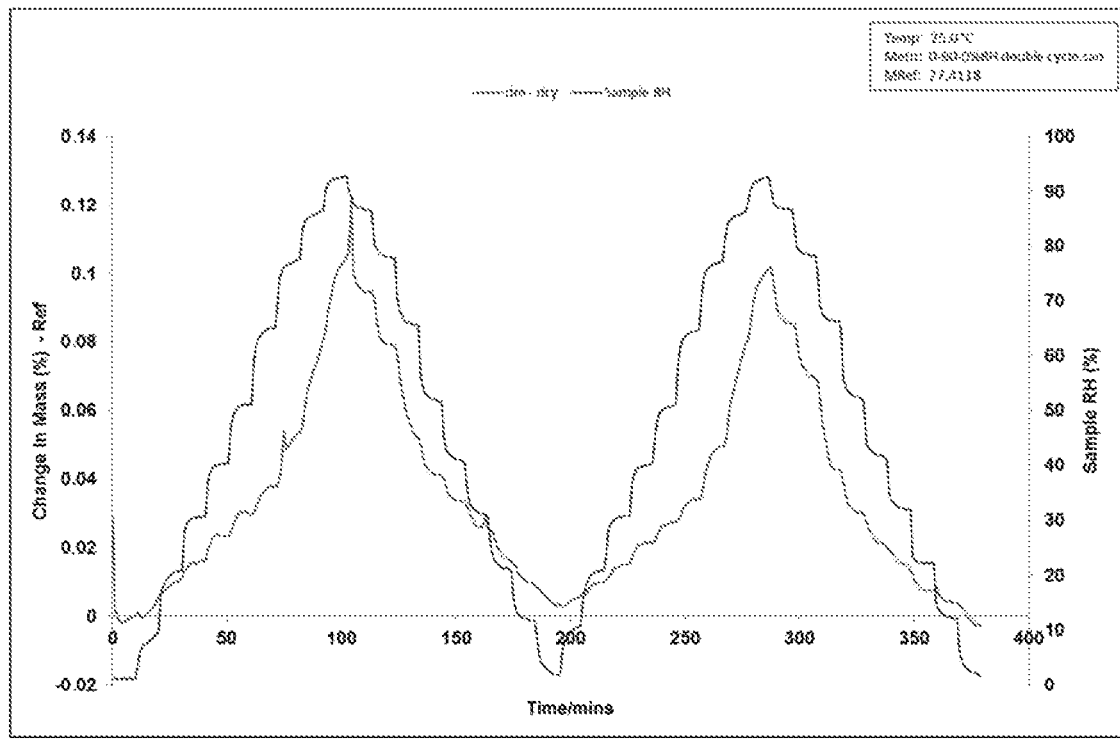
FIG. 42 shows a DVS change in mass plot of a diethylamine salt Formula 2 from a second preparation of KM-819.
Figure 43:
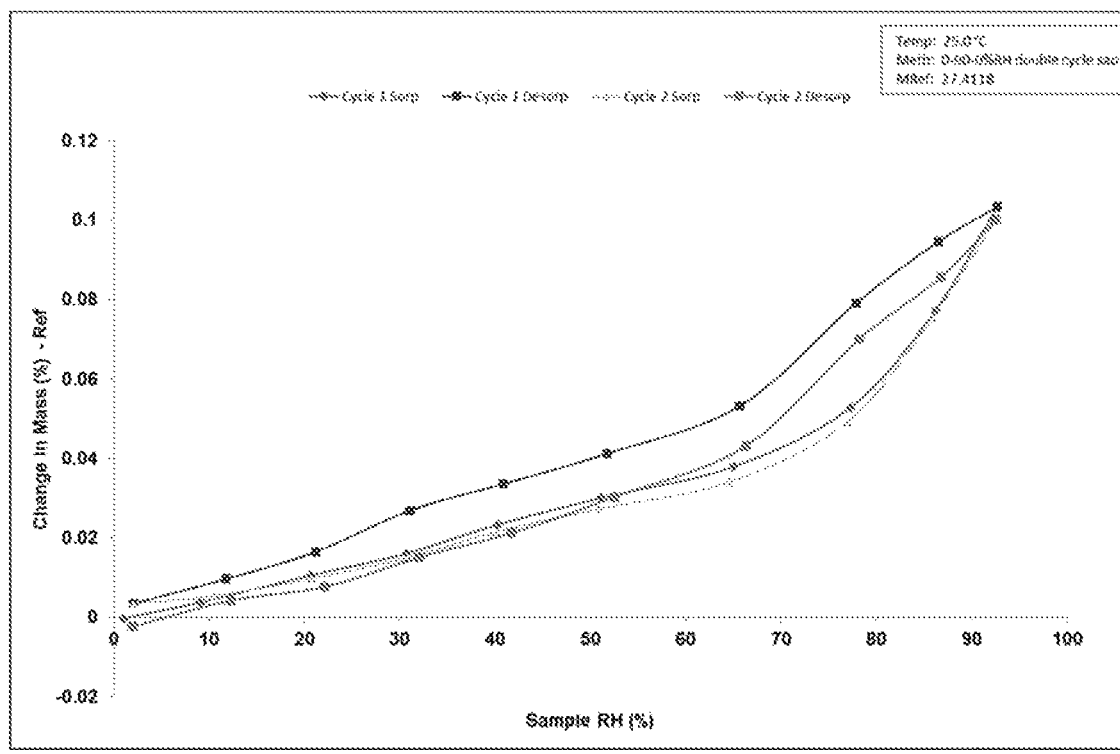
FIG. 43 shows a DVS isotherm plot of a diethylamine salt Formula 2 from a second preparation of KM-819.
Figure 44:
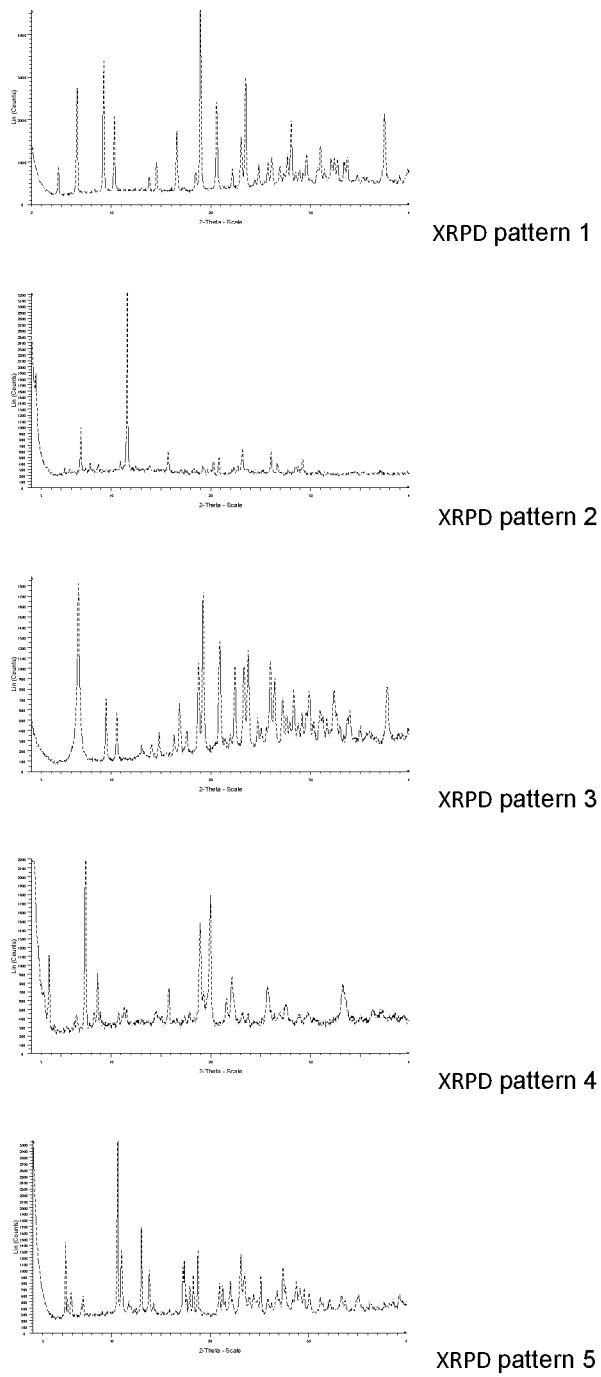
FIG. 44 shows an alignment of the five XRPD diffraction patterns of salts obtained during the screen. Spectra are aligned by the 2-theta scale.
Figure 45:
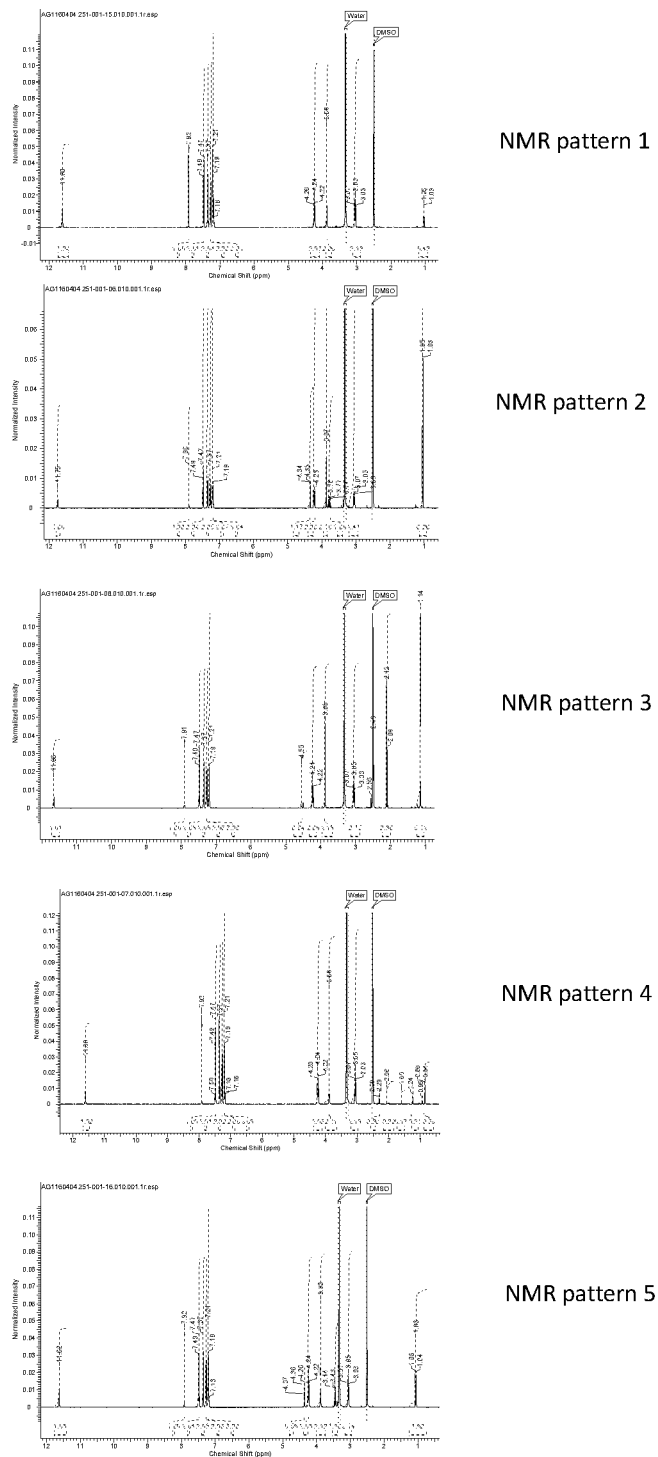
FIG. 45 shows an alignment of five distinct 1H NMR analyses observed in samples from the salt screen. The spectra are aligned via the DMSO standard peak. Pattern numbering corresponds to the numbering of the XRPD patterns, thus salts exhibiting the XRPD pattern 1 will often exhibit NMR pattern 1 as well.

Solubility assessment of the Compound 1 (KM-00819) was performed using water and a diverse range of organic solvents. A list of solvents suitable for use during a salt screen was determined from this assessment. At the completion of the solvent screen 1.1 eq of NaOH(aq) was added to each of the samples in order to test the ability of the samples to generate a salt form. Upon addition of the hydroxide, cloudy precipitates were formed from some samples indicating that salt formation may have occurred, and on XRPD analysis of solids isolated from salt formation, 5 distinct diffraction patterns were observed. (See, e.g., Example 8 and FIGS. 10-19 and 44.) 1H NMR analysis of samples showing diffraction patterns was used to determine which solvents would be the most suitable for use in preparing salt forms of KM-819 as explained below. FIG. 45 shows an alignment of representative 1H NMR analyses of samples from the salt screen.

Salt Screen

The salt screen was performed using approximately 25 mg of the compound 1 (KM-819) per experiment with 3 solvents and 22 bases, which were added in a ratio of 1:1.1 (free acid:base). Upon preparation the samples were matured for 5 days prior to filtration and analysis by XRPD. In instances when the salt remained completely soluble the solvent was slowly evaporated from the sample.

Aqueous solubility assessment of the salts exhibiting novel XRPD patterns was performed and any that showed complete or partial dissolution after being shaken overnight at 50° C. (at a concentration of 1.25 mg/ml) were further analyzed by 1H NMR. Some salts exhibited polymorphism as shown by differences in XRPD pattern and 1H NMR chemical shifts.

Disclosed herein are new pharmaceutically acceptable solid forms of KM-819 and salts thereof and processes of their preparation. These forms can be used to prepare salts or base and prepare formulations thereof for clinical use.

Disclosed herein are new pharmaceutically acceptable salts of 4-(2-((4-bromophenyl)thio)acetamido)-1-phenethyl-1H-pyrazole-3-carboxylic acid (KM-819) in crystalline or amorphous form and methods of their production. These salts can be used to prepare other salt or free base forms of KM-819 and to prepare formulations thereof for clinical use.

The present invention relates to salt and/or solvate (hydrate) compounds according to Formula 2 below.

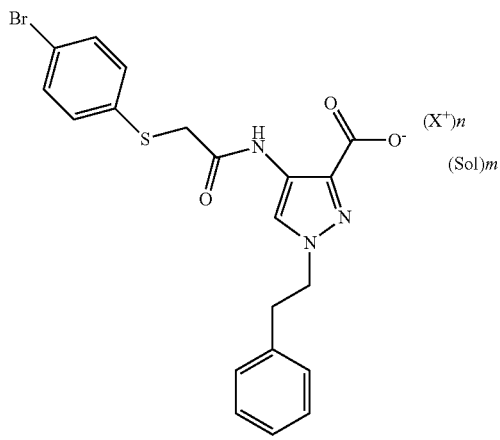 [SMILES: O=C(CSc1ccc(Br)cc1)Nc1cn(CCc2ccccc2)nc1C(=O)[O-]]

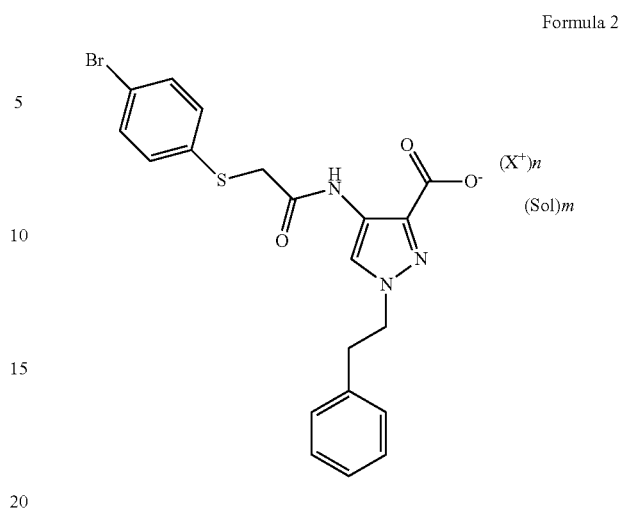

Structure of salt of KM-819 (Formula 2 or Salt Compound 2)

In Formula 2, n is an integer 1, 2 or 3;

m is from 0 to 3 and can be a non-integer, for example 0.5 or 1.5;

"Sol" is a solvent molecule and can be, for example, water or C2-C4 alcohol; and X+ is a cation, and can be, for example, a potassium ion, a sodium ion, a calcium ion, magnesium ion, ammonium ion or a substituted ammonium ion.

A salt compound of the Formula 2 can be prepared by treating the free base or zwitterion of Compound 1 with, for example, potassium hydroxide, sodium hydroxide, L-arginine, calcium hydroxide, N,N,N-trimethylglycine, ammonium hydroxide, magnesium hydroxide, choline, diethylamine, L-lysine, N,N'-dibenzylethylenediamine, N-ethylglucamine, calcium acetate, 1-(2-hydroxyethyl)pyrrolidine, N-(phenylmethyl)benzeneethaneamine, ammonia, magnesium acetate, N-methylglucamine, tromethamine, 4-(2-hydroxyethyl)morpholine, 2-(diethylamino)ethanol, or 2-dimethylamino-ethanol.

In some instances of a salt compound of Formula 2 m can be 0.5 or 1. In some such instances, X+ can be potassium ion, sodium ion or quaternary methylamine or quaternary ethylamine.

Salt Compounds 2 can alternatively or additionally be in the form of solvates such as those including water, ethanol or diisopropyl ether, or a mixture of any two or three of them. The solvent molecule can be present in a non-integer ratio to either or both of water molecules and the compound 1 ion, for example 0.1, 0.2, or 0.5 solvent molecules per molecule of compound 1 ion. The solvent molecule can be present in an integer ratio to either or both of water molecules and the compound 1 ion, for example 1 or 2 solvent molecules per molecule of compound 1 ion.

Also disclosed is a process for preparing the salt compound of Formula 2:

wherein:

n is 1, 2 or 3;

m is 0 to 3;

X+ is a cation;

"Sol" is a solvent molecule;

the process comprising:
i) dissolving the free acid form of a compound of formula 2 in an organic solvent or in an organic solvent mixed with water;
ii) adding an excess over the stoichiometric amount of a base required to titrate the free acid compound of formula 2 to form a precipitate of the salt compound of formula 2; and
iii) collecting the precipitate to obtain the salt compound 2.

In such a process, the organic solvent can be 1,1-dimethoxyethane, acetonitrile, ethanol, 1,2-dichloroethane, benzonitrile, ethyl acetate, 1,4-dioxane, anisole, heptane, 2-butanol, cumene, hexane, 2-propanol, cyclohexane, isopropyl acetate, 4-methyl-pentan-2-one, dichloromethane, methanol, acetone, diisopropyl ether (DIPE), isobutyl acetate, tetralin, toluene, methylethyl ketone (MEK), N-methylpyrrolidone, tert-butylmethyl ether (TMBE), nitromethane, pyridine or tetrahydrofuran, or a mixture of any two or three of them.

In some implementations of the process, the organic solvent can be ethanol or diisopropyl ether (DIPE).

In some implementations of the process, the base can be sodium hydroxide, potassium hydroxide, magnesium hydroxide, magnesium acetate, ammonia, a salt of quaternary dimethylamine or a salt of quaternary diethylamine.

A combination of use of ethanol or DIPE as the organic solvent and sodium hydroxide, potassium hydroxide or a salt of quaternary dimethylamine or a salt of quaternary diethylamine as the base can also be used.

In some instances ethanol or DIPE is used as the organic solvent.

Water can be mixed with the organic solvent, and in some instances water can be mixed with ethanol or DIPE.

In any implementation in which water is mixed with an organic solvent, e.g. when water is mixed with a polar organic solvent, the ratio of water to polar organic solvent can range from 5:1 to 10:0.1.

The free base (or zwitterionic) Compound 1 can be dissolved in unbuffered water, a range of organic solvents, mixtures of organic solvents and mixtures of solvents with unbuffered water. The solvents assessed were 1,1-dimethoxyethane, acetonitrile, ethanol, 1,2-dichloroethane, benzonitrile, ethyl acetate, 1,4-dioxane, anisole, heptane, 2-butanol, cumene, hexane, 2-propanol, cyclohexane, isopropyl acetate, 4-methyl-pentan-2-one, dichloromethane, methanol, acetone, diisopropyl ether (DIPE), isobutyl acetate, tetralin, toluene, methylethyl ketone, N-methylpyrrolidone, tert-butylmethyl ether, nitromethane, pyridine, tetrahydrofuran. Results of example solubility tests are shown in Table 2 below.

Organic solvents can be used neat, or as a mixture of two or three or more organic solvents. Water alone can be used as a solvent for the free base (or zwitterionic) Compound 1, or water can be mixed together with one or more organic solvents. Preferably neat polar organic solvent or solvent mixture, or an aqueous mixture of a polar organic solvent, is used to dissolve the free base or zwitterionic Compound 1.

In the instance of a binary mixture, a ratio of water to organic solvent (preferably a polar organic solvent) in a solvent mixture can be from 1:10 to 1:0.1, or from 1:5-1:0.1, or from 1:2-1:0.1, or from 1:2-1:0.5, or about 1:1.

Salt Formation

The general methods for preparing the salt compounds of this disclosure are illustrated in the following Scheme.

Scheme 1 shows the synthesis of salt forms following a general route that utilizes well-established chemistry.

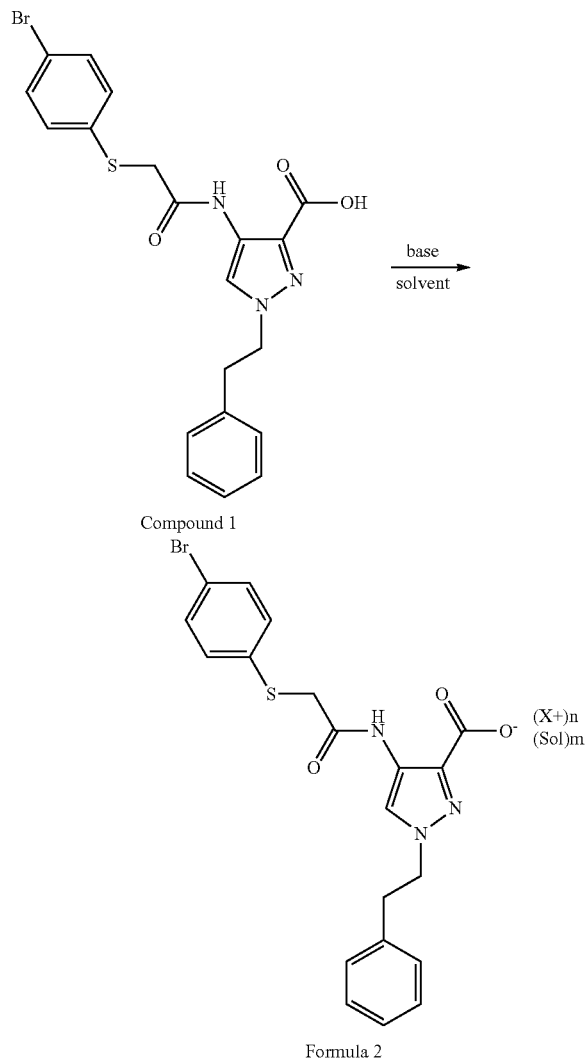

Scheme 1

Compound 1

Formula 2

The free acid Compound 1 is weighed and added to a vessel and then solvent is added to the vessels. About 1.1 eq of the base prepared as a 1M stock solutions in solvent is then added. Clouding of the sample upon base addition indicates that salt formation is occurring. Post-maturation (standing for several hours at room temperature), the samples were filtered and dried in vacuo and then characterized by various methods.

The base used for salt formation can be potassium hydroxide, sodium hydroxide, L-arginine, calcium hydroxide, N,N,N-trimethylglycine, ammonium hydroxide, magnesium hydroxide, choline, diethylamine, L-lysine, N,N'-dibenzylethylenediamine, N-ethylglucamine, calcium acetate, 1-(2-hydroxyethyl)pyrrolidine, N-(phenylmethyl)benzeneethaneamine, ammonia, magnesium acetate, N-methylglucamine, tromethamine, 4-(2-hydroxyethyl)morpholine, 2-(diethylamino)ethanol or 2-dimethylaminoethanol.

Many organic compounds exist in different solid forms that can be amorphous or in a crystalline state.

The ability of a compound to crystallize in different crystalline phases is called polymorphism. The term polymorph may include the amorphous phases (disordered), hydrates (water presents in the crystal lattice) and solvates (solvents other than water present in the crystal lattice).

Different crystalline modifications have different crystal structures and different free energies, therefore polymorphs exhibit different physico-chemical properties such as melting point, density, solubility, chemical stability and finally, bioavailability.

Examples of preferred salts of 4-(2-((4-bromophenyl)thio)acetamido)-1-phenethyl-1H-pyrazole-3-carboxylic acid of the salt Compound 2 are:

The salt of 4-(2-((4-bromophenyl)thio)acetamido)-1-phenethyl-1H-pyrazole-3-carboxylic acid and potassium hydroxide;

The salt of 4-(2-((4-bromophenyl)thio)acetamido)-1-phenethyl-1H-pyrazole-3-carboxylic acid and sodium hydroxide;

The salt of 4-(2-((4-bromophenyl)thio)acetamido)-1-phenethyl-1H-pyrazole-3-carboxylic acid and ammonium hydroxide;

The salt of 4-(2-((4-bromophenyl)thio)acetamido)-1-phenethyl-1H-pyrazole-3-carboxylic acid and choline;

The salt of 4-(2-((4-bromophenyl)thio)acetamido)-1-phenethyl-1H-pyrazole-3-carboxylic acid and diethylamine;

The salt of 4-(2-((4-bromophenyl)thio)acetamido)-1-phenethyl-1H-pyrazole-3-carboxylic acid and L-lysine;

The salt of 4-(2-((4-bromophenyl)thio)acetamido)-1-phenethyl-1H-pyrazole-3-carboxylic acid and N,N'-dibenzylethylenediamine;

The salt of 4-(2-((4-bromophenyl)thio)acetamido)-1-phenethyl-1H-pyrazole-3-carboxylic acid and N-ethylglucamine;

The salt of 4-(2-((4-bromophenyl)thio)acetamido)-1-phenethyl-1H-pyrazole-3-carboxylic acid and calcium acetate;

The salt of 4-(2-((4-bromophenyl)thio)acetamido)-1-phenethyl-1H-pyrazole-3-carboxylic acid and N-(phenylmethyl)benzeneethaneamine;

The salt of 4-(2-((4-bromophenyl)thio)acetamido)-1-phenethyl-1H-pyrazole-3-carboxylic acid and magnesium acetate;

The salt of 4-(2-((4-bromophenyl)thio)acetamido)-1-phenethyl-1H-pyrazole-3-carboxylic acid and N-methylglucamine;

The salt of 4-(2-((4-bromophenyl)thio)acetamido)-1-phenethyl-1H-pyrazole-3-carboxylic acid and tromethamine; and The salt of 4-(2-((4-bromophenyl)thio)acetamido)-1-phenethyl-1H-pyrazole-3-carboxylic acid and 4-(2-hydroxyethyl)morpholine.

Many solids isolated from the salt forming step exhibited diffraction patterns in XRPD analysis (indicating the solid is crystalline), and some exhibited different diffraction patterns from that of the free acid Compound 1. 1H NMR analysis of crystalline solids in many cases showed that the —COOH group in the Compound 1 had ionized.

Preferable solvents suitable for use in salt formation are those that completely dissolve the free acid Compound 1 and preferable bases for use in preparing salt Compound 2 from Compound 1 are those in which the base completely replaces the carboxylate hydrogen of Compound 1.

Abbreviations

| | | | |
|---|---|---|---|
| λ | Wavelength | Ltd | Limited |
| % | Percentage | M | Moles |
| Θ | Theta | mA | Milliamp |
| % RH | Percentage relative humidity | MeOH | Methanol |
| % RSD | Percentage relative standard deviation | mg | Milligram |
| ° C. | Degree centigrade | mg/mL | Milligrams per milliliter |
| ° C./min | Degree centigrade per minute | mJ | Millijoule |
| μL | Microliters | mL | Milliliter |
| μm | Microns | mL/min | Milliliter per minute |
| API | Active pharmaceutical ingredient | mM | millimolar |
| ATR | Attenuated total reflection | mm | Millimeter |
| Ca. | Approximately | mm/s | Millimeter per second |
| CCD | Charge-coupled device | MP | Megapixels |
| $cm^{-1}$ | Wave number | mW | Milliwatt |
| d-DMSO | Duterated dimethyl sulfoxide | nm | nanometer |
| DIPE | Diisopropyl ether | PC | Personal computer |
| DSC | Differential scanning calorimetry | pH | Potential of Hydrogen |
| DVS | Dynamic vapour sorption | PLM | Polarised light microscopy |
| eq | Equivalents | PPM | Parts per million |
| FASSIF | Fasted state simulated intestinal fluid | QNP | Quadruple nucleus probe |
| FESSIF | Fed state simulated intestinal fluid | RT | Room temperature |
| FT-IR | Fourier transform infrared spectroscopy | SCXRD | Single crystal X-ray diffraction |
| g | Gram | Std Dev | Standard deviation |
| h | Hours | TGA | Thermogravametric analysis |
| 1H NMR | Proton nuclear magnetic resonance | VMD | Volume mean diameter |
| HPLC | High performance liquid chromatography | Wt % | Weight Percentage |
| HSM | Hot stage microscopy | X10 | 10% of particles |
| ICP | Inductively coupled plasma | X50 | 50% of particles |
| J/g | Joule/gram | X90 | 90% of particles |
| kV | Kilovolt | XRPD | X-ray powder diffraction |

EXAMPLES

The following examples describe preparation and detailed characterization of representative embodiments.

4-(2-((4-bromophenyl)thio)acetamido)-1-phenethyl-1H-pyrazole-3-carboxylic acid (Compound 1) was synthesized as described by WO2008/051047 to obtain a white, crystalline powder.

Samples for the Examples were synthesized by the disclosed method (Example 1, 2, 4, 5) and analyzed by XRPD, 1H NMR, HPLC chemical purity and solubility.

Instrumentation

Perkin Elmer PYRIS 1 DSC using 40 μL aluminium pans (vented). Data collections and analysis was performed using the Perkin Elmer control and analysis software v11.0.2.0468

Bruker 400 Avance spectrometer equipped with a 5 mm QNP probe. Instrument control and data collection was performed using Top Spin v1.3 with the analysis being performed using ACD Laboratories 1D NMR processor v. 12.01.

Jasco 420 FTIR using attenuated total reflectance (ATR) module. Analysis and data collection was performed using the Jasco Spectra Manager software v1.51.00 (Build 1).

Olympus BX53 microscope equipped for polarised light microscopy with 6 objective lenses (2.5×, 4×, 10×, 20×, 40× and 100×) and 1/10λ wave plate. Sony ICX252 progressive scan interline 3.3MP CCD camera. The microscope was also equipped with a Linkam LTS420 heating/freezing stage.

PLM: Data analysis and image capture via Qcapture-Pro v7 imaging software.

HSM: Data analysis and image capture via Linksys 32DV temperature control and digital video capture software.

Bruker-AXS D8 Advance XRPD using 9 mm cavity and flat plate sample holders. Instrument control and data collection was performed using a PC equipped with Diffrac Plus XRD Commander control software v2.6.1 and analysis of the recorded data was performed Eva v18,0,0,0.

SMS DVS Intrinsic dynamic vapour sorption instrument using DVS-Intrinsic control software v1.0.6.0. Analysis of the data was performed using the DVS analysis suite v7.0.13.1 macro program embedded in Microsoft Excel. Analysis was performed as a wt % change from 0-90% RH with isothermal plots also being examined.

Perkin Elmer PYRIS 1 TGA using aluminium pans (vented) in ceramic crucibles. Data analysis and collection was performed using the Perkin Elmer control and analysis software v11.0.2.0468.

Thermo-Fisher iCAP 6500 ICP-OES using iTEVA software.

Metrohm 852 Titranto combined Volumetric and Coulometric KF unit. All samples were analyzed using volumetric Karl Fischer module.

Waters-Alliance 2695 HPLC spectrometer equipped with a PDA 2996 probe. System control and processing was performed with Empower 3 software Build 3471.

HeidolphTitramax 1000 with heating module.

Example 1

4-(2-((4-bromophenyl)thio)acetamido)-1-phenethyl-1H-pyrazole-3-carboxylic acid potassium salt Ca. 25 mg of the compound 1 (KM-00819) was weighed into a 2 mL HPLC vial prior to the addition of 1500 μL. To the resulting slurries was added 1.1 eq of potassium hydroxide in 60 ul in water (to 1M concentration). The sample was placed on to a maturation cycle for 5 days using an 8 hour cycle (4 hours at RT followed by 4 hours at 50° C.). Post-maturation the sample was re-examined and then filtered and dried in vacuo.

Example 2: 4-(2-((4-bromophenyl)thio)acetamido)-1-phenethyl-1H-pyrazole-3-carboxylic Acid Calcium Salt Ca. 25 mg of the compound 1 (KM-00819) was weighed into a 2 mL HPLC vial prior to the addition of 1500 μL of a solvent as set forth in Table 1. To the resulting slurries was added 1.1 eq of Calcium hydroxide (5.6 μg) as solid. The sample was placed on to a maturation cycle for 5 days using an 8 hour cycle (4 hours at RT followed by 4 hours at 50° C.). Post-maturation the sample was re-examined and then filtered and dried in vacuo.

Example 3: Additional salts of 4-(2-((4-bromophenyl)thio)acetamido)-1-phenethyl-1H-pyrazole-3-carboxylic Acid The following salts of compound were prepared by same the method as Example 1 or Example 2:

TABLE 1

Formation of salts

| Salt Former | Amount of Base Added (1M soln) or solid | Solvent | Synthetic Method (General Method) |
|---|---|---|---|
| Potassium hydroxide | 60 μL | Ethanol | EXAMPLE 1 |
| Sodium hydroxide | 60 μL | Ethanol | EXAMPLE 1 |
| L-Arginine | 11.12 μg | Ethanol | EXAMPLE 2 |
| Calcium hydroxide | 5.6 μg | Ethanol | EXAMPLE 2 |
| N,N,N-Trimethylglycine | 60 μL | Ethanol | EXAMPLE 1 |
| Ammonium hydroxide | 60 μL | Ethanol | EXAMPLE 1 |
| Magnesium hydroxide | 4.6 μg | Ethanol | EXAMPLE 2 |
| Choline | 60 μL | Ethanol | EXAMPLE 1 |
| Diethylamine | 60 μL | Ethanol | EXAMPLE 1 |
| L-Lysine | 60 μL | Ethanol | EXAMPLE 1 |
| N,N'-Dibenzylethylenediamine | 60 μL | Ethanol | EXAMPLE 1 |
| N-Ethylglucamine | 60 μL | Ethanol | EXAMPLE 1 |
| Calcium acetate | 60 μL | Ethanol | EXAMPLE 1 |
| 1-(2-Hydroxyethyhpyrrolidine | 60 μL | Ethanol | EXAMPLE 1 |
| N-(Phenylmethyl) benzeneethaneamine | 60 μL | Ethanol | EXAMPLE 1 |
| Ammonia | 60 μL | Ethanol | EXAMPLE 1 |
| Magnesium acetate | 60 μL | Ethanol | EXAMPLE 1 |
| N-Methylglucamine | 60 μL | Ethanol | EXAMPLE 1 |
| Tromethamine | 60 μL | Ethanol | EXAMPLE 1 |
| 4-(2-hydroxyethyl)morpholine | 60 μL | Ethanol | EXAMPLE 1 |
| 2-(Diethylamino)ethanol* | 60 μL | Ethanol | EXAMPLE 1 |
| 2-Dimethylamino-ethanol* | 60 μL | Ethanol | EXAMPLE 1 |
| Potassium hydroxide | 60 μL | Diisopropyl Ether | EXAMPLE 1 |
| Sodium hydroxide | 60 μL | Diisopropyl Ether | EXAMPLE 1 |
| L-Arginine | 11.0 μg | Diisopropyl Ether | EXAMPLE 2 |
| Calcium hydroxide | 5.2 μg | Diisopropyl Ether | EXAMPLE 2 |
| N,N,N-Trimethylglycine | 60 μL | Diisopropyl Ether | EXAMPLE 1 |
| Ammonium hydroxide | 60 μL | Diisopropyl Ether | EXAMPLE 1 |
| Magnesium hydroxide | 3.8 μg | Diisopropyl Ether | EXAMPLE 2 |
| Choline | 60 μL | Diisopropyl Ether | EXAMPLE 1 |
| Diethylamine | 60 μL | Diisopropyl Ether | EXAMPLE 1 |
| L-Lysine | 60 μL | Diisopropyl Ether | EXAMPLE 1 |
| N,N'-Dibenzylethylenediamine | 60 μL | Diisopropyl Ether | EXAMPLE 1 |
| N-Ethylglucamine | 60 μL | Diisopropyl Ether | EXAMPLE 1 |
| Calcium acetate | 60 μL | Diisopropyl Ether | EXAMPLE 1 |
| 1-(2-Hydroxyethyhpyrrolidine | 60 μL | Diisopropyl Ether | EXAMPLE 1 |
| N-(Phenylmethyl) benzeneethaneamine | 60 μL | Diisopropyl Ether | EXAMPLE 1 |
| Ammonia | 60 μL | Diisopropyl Ether | EXAMPLE 1 |
| Magnesium acetate | 60 μL | Diisopropyl Ether | EXAMPLE 1 |
| N-Methylglucamine | 60 μL | Diisopropyl Ether | EXAMPLE 1 |
| Tromethamine | 60 μL | Diisopropyl Ether | EXAMPLE 1 |
| 4-(2-hydroxyethyl)morpholine | 60 μL | Diisopropyl Ether | EXAMPLE 1 |
| 2-(Diethylamino)ethanol* | 60 μL | Diisopropyl Ether | EXAMPLE 1 |
| 2-Dimethylamino-ethanol* | 60 μL | Diisopropyl Ether | EXAMPLE 1 |
| Potassium hydroxide | 60 μL | 4-Methylpentan-2-one | EXAMPLE 1 |
| Sodium hydroxide | 60 μL | 4-Methylpentan-2-one | EXAMPLE 1 |
| L-Arginine | 16.8 μg | 4-Methylpentan-2-one | EXAMPLE 2 |
| Calcium hydroxide | 5.3 μg | 4-Methylpentan-2-one | EXAMPLE 2 |
| N,N,N-Trimethylglycine | 60 μL | 4-Methylpentan-2-one | EXAMPLE 1 |
| Ammonium hydroxide | 60 μL | 4-Methylpentan-2-one | EXAMPLE 1 |
| Magnesium hydroxide | 3.8 μg | 4-Methylpentan-2-one | EXAMPLE 2 |
| Choline | 60 μL | 4-Methylpentan-2-one | EXAMPLE 1 |
| Diethylamine | 60 μL | 4-Methylpentan-2-one | EXAMPLE 1 |
| L-Lysine | 60 μL | 4-Methylpentan-2-one | EXAMPLE 1 |
| N,N'-Dibenzylethylenediamine | 60 μL | 4-Methylpentan-2-one | EXAMPLE 1 |
| N-Ethylglucamine | 60 μL | 4-Methylpentan-2-one | EXAMPLE 1 |
| Calcium acetate | 60 μL | 4-Methylpentan-2-one | EXAMPLE 1 |

TABLE 1-continued

Formation of salts

| Salt Former | Amount of Base Added (1M soln) or solid | Solvent | Synthetic Method (General Method) |
|---|---|---|---|
| 1-(2-Hydroxyethyhpyrrolidine | 60 μL | 4-Methylpentan-2-one | EXAMPLE 1 |
| N-(Phenylmethyl) benzeneethaneamine | 60 μL | 4-Methylpentan-2-one | EXAMPLE 1 |
| Ammonia | 60 μL | 4-Methylpentan-2-one | EXAMPLE 1 |
| Magnesium acetate | 60 μL | 4-Methylpentan-2-one | EXAMPLE 1 |
| N-Methylglucamine | 60 μL | 4-Methylpentan-2-one | EXAMPLE 1 |
| Tromethamine | 60 μL | 4-Methylpentan-2-one | EXAMPLE 1 |
| 4-(2-hydroxyethyl)morpholine | 60 μL | 4-Methylpentan-2-one | EXAMPLE 1 |
| 2-(Diethylamino)ethanol* | 60 μL | 4-Methylpentan-2-one | EXAMPLE 1 |
| 2-Dimethylamino-ethanol* | 60 μL | 4-Methylpentan-2-one | EXAMPLE 1 |

*Note: after 3 days maturation these samples were observed to be completely soluble at RT so were slowly evaporated over 3 days in an attempt to generate crystals.

Example 4: 4-(2-((4-bromophenyl)thio)acetamido)-1-phenethyl-1H-pyrazole-3-carboxylic Acid Sodium Salt Ca. 1 g of the compound 1 was weighed into 3×100 mL vials prior to the addition of 60 mL of DIPE to each of the vessels. To the resulting suspension was added 1.1 eq of sodium hydroxide which had been prepared as 1M stock solution in water. On base addition, the reaction mixture was observed to become cloudier, which indicates that salt formation was occurring. Post-maturation (as in Example 1) the samples were filtered and dried in vacuo.

Example 5: 4-(2-((4-bromophenyl)thio)acetamido)-1-phenethyl-1H-pyrazole-3-carboxylic Acid Potassium Salt The salt of 4-(2-((4-bromophenyl)thio)acetamido)-1-phenethyl-1H-pyrazole-3-carboxylic acid and potassium hydroxide was prepared by using procedures analogous to those described in Example 4.

Example 6: 4-(2-((4-bromophenyl)thio)acetamido)-1-phenethyl-1H-pyrazole-3-carboxylic Acid and Diethylamine The salt of 4-(2-((4-bromophenyl)thio)acetamido)-1-phenethyl-1H-pyrazole-3-carboxylic acid and diethylamine was prepared by using procedures analogous to those described in Example 4.

Example 7: 4-(2-((4-bromophenyl)thio)acetamido)-1-phenethyl-1H-pyrazole-3-carboxylic Acid and Diethylamine Ca. 8 g of the free acid of Compound 1 was weighed into a 500 mL glass vessel prior to the addition of 480 mL of DIPE. To the resulting suspension was added 1.1 eq of diethylamine which had been prepared as 1M stock solution in DIPE. On base addition the sample was observed to settle out of the reaction mixture indicating that salt formation had occurred. Maturation of the sample was then performed for 4 days (8 hour cycles of 4 hours at 50° C. and 4 hours at RT). Post-maturation the sample was filtered and dried in vacuo at 40° C. for 2 days.

Example 8: Solubility in Various Solvents

Ca. 10 mg of the free acid of Compound 1 was weighed into 2 mL HPLC vials prior to the addition of solvent in 100-250 μL increments up to a maximum of 1750 μL. After each addition of solvent the samples were briefly shaken to encourage dissolution and visually inspected for signs of any remaining solid. Once the maximum volume of solvent had been added, 1.1 eq of 1M NaOH(aq) solution was also added, to give an indication as to which of the solvents would yield a suitable salt form. The samples were visually inspected prior to maturation for 2 days, after which all were inspected again. All the samples were then left to evaporate at RT to generate solid material.

Analysis of the recovered solid by XRPD post maturation showed there was a frequently observed diffraction pattern (Pattern 1) that is observed for the sodium salt prepared from most of the solvents tested. However, four additional patterns were also identified less commonly. Salts exhibiting these five patterns were further analysed by 1H NMR from which the following conclusions have been drawn:

pattern 1: Crystalline sodium salt (from the majority of solvents tested)
pattern 2: Solvate of the sodium salt (from 2-butanol and 2-propanol)
pattern 3: Possible new polymorph (from 4-methyl-pentan-2-one)
pattern 4: Sodium salt with unknown contamination (from acetone)
pattern 5: Hemi-ethanoate of the sodium salt (from ethanol).

The following list of peaks can be used to distinguish one of these patterns from another. Values of 2-theta are rounded to two decimal places.

Pattern 1 is characterized by peaks at 2-theta of 4.68, 6.54, 9.24, 10.30, 13.80, 14.54, 16.60, 18.48, 18.96, 20.60, 22.18, 23.04, 23.49, 24.83, 25.76, 26.15, 26.97, 27.72, 28.09, 28.91, 29.63, 30.71, 31.03, 31.41, 32.10, 32.45, 32.75, 33, 48, 33.76 and 34.74.

Pattern 2 is characterized by peaks at 2-theta of 7.00, 11.61, 15.75, 19.19, 20.30, 20.86, 23.19, 26.08, 26.72 and 29.29.

Pattern 3 is characterized by peaks at 2-theta of 6.71, 9.47, 10.59, 13.13, 14.06, 14.86, 16.30, 16, 90, 17.64, 18.81, 19.28, 20.92, 22.49, 23.39, 23.80, 24.73, 25.12, 26.05, 26.45, 27.27, 27.66, 28.35, 28.79, 29.20, 29.92, 31.00, 32.46, 34.01 and 35.09.

Pattern 4 is characterized by peaks at 2-theta of 3.76, 6.47, 7.46, 8.28, 8.63, 11.34, 14.49, 15.78, 18.96, 19.27, 19.97, 21.64, 22.16, 23.24, 25.67, 27.61, 29.77 and 33.27.

Pattern 5 is characterized by peaks at 2-theta of 5.30, 5.83, 7.09, 10.57, 10.97, 11.75, 13.02, 13.80, 17.38, 17.97, 18.23, 18.75, 21.26, 22.10, 23.13, 23.50, 25.17, 26.84, 27.39, 28.76, 29.14, 29.57, 30.05, 31.18, 32.15, 33.44, 35.06, 36.29 and 39.26.

Table 2 shows the results of the solubility screen.

TABLE 2

Solubility Screen

| Solvent | Solvent Addition (µL) | Observation on Addition of 1.1eq of NaOH | Observation Post Maturation | XRPD Results |
|---|---|---|---|---|
| 1,1-Dimethoxyethane | 1750 | White PPT formed | Clear liquid with fluffy solid & powered sediment | Crystalline-Pattern 1 |
| 1,2-Dichloroethane | 1750 | No change | Clear liquid with gelatinous solid & suspensions | Crystalline-Pattern 1 |
| 1,4-Dioxane | 750 | No change | Clear liquid | No solids |
| 2-Butanol | 1750 | No change | Clear liquid with fluffy solid & powered sediment | Crystalline-Pattern 2 |
| 2-Propanol | 1750 | No change | Clear liquid & white solid | Crystalline-Pattern 2 |
| 4-methyl-pentan-2-one | 1750 | No change | Clear liquid & white solid | Crystalline-Pattern 3 |
| Acetone | 1750 | Clear liquid & white PPT | Clear liquid & needles | Crystalline-Pattern 4 |
| Acetonitrile | 1750 | No change | Clear liquid & gelatinous solid | Crystalline-Pattern 1 |
| Benzonitrile | 1750 | No change | Hazy suspension & some solids | Partially Crystalline |
| Anisole | 1750 | No change | White solid sediment and & some gelatinous solid | Crystalline-Pattern 1 |
| Cumene | 1750 | No change | Clear liquid & white solid | Crystalline-Pattern 1 |
| Cyclohexane | 1750 | No change | Hazy suspension/clear liquid | Crystalline-Pattern 1 |
| Dichloromethane | 1750 | No change | Clear liquid & gelatinous solid | Crystalline-Pattern 1 |
| Diisopropyl ether | 1750 | No change | Clear liquid & white solid | Crystalline-Pattern 1 |
| Ethanol | 1750 | No change | Clear liquid & white solid | Crystalline-Pattern 5 |
| Ethyl acetate | 1750 | No change | Clear liquid & white solid | Crystalline-Pattern 1 |
| Heptane | 1750 | No change | Hazy suspension & white solid | Crystalline-Pattern 1 |
| Hexane | 1750 | No change | Hazy suspension & white solid | Crystalline-Pattern 1 |
| Isopropyl acetate | 1750 | No change | Clear liquid & white solid | Crystalline-Pattern 1 |
| Methanol | 1750 | Clear liquid & white PPT | Clear liquid | No solids |
| Isobutyl Acetate | 1750 | No change | Clear liquid & white solid | Crystalline-Pattern 1 |
| Methylethyl ketone | 1750 | No change | Clear liquid & gelatinous solid | Partially Crystalline-Pattern 1 |
| Nitromethane | 1750 | No change | Yellow liquid & white solid | Crystalline-Pattern 1 |
| N-Methylpyrrolidone | 250 | No change | Pale yellow liquid | No solids |
| Pyridine | 1750 | No change | Pale yellow liquid | No solids |
| tert-Butylmethyl ether | 1750 | No change | Clear liquid & white solid | Crystalline-Pattern 1 |
| Tetrahydrofuran | 750 | No change | Clear liquid | No solids |
| Tetralin | 1750 | No change | Hazy suspension & white solid | Partially Crystalline-Pattern 1 |
| Toluene | 1750 | No change | Clear liquid & gelatinous solid | Crystalline-Pattern 1 |
| Water | 1750 | No change | Clear liquid & gelatinous solid | Partially Crystalline |

Example 9: Powder X-Ray Diffraction (XRPD) Analysis

Samples were prepared by coating them onto sample holders fitted with a zero background silicon wafer (5 1 0). Analysis was performed using a Cu Kα X-Ray source which operated at 40 kV at 40 mA and a LynxEye™ detector; all samples were analyzed over the range 2-40° 2θ.

XRPD analysis indicated that the salts had generated crystalline solids with novel crystalline patterns compared to the free acid Compound 1 with a further sample giving a partially crystalline pattern (see Table 3 and FIGS. 1-19 and 44).

TABLE 3

XRPD assessment on solid samples isolated from the salt screen

| Salt Former | From Ethanol XRPD Analysis | From DIPE XRPD Analysis | From MIBK XRPD Analysis |
| --- | --- | --- | --- |
| Potassium hydroxide | Crystalline: Pattern 1 | Crystalline: Pattern 2 | Crystalline: Pattern 3 (similar to Pattern 2) |
| Sodium hydroxide | Crystalline: Pattern 1 | Crystalline: Pattern 2 | Crystalline: Pattern 2 |
| L-Arginine | Oil | Starting material | Starting material |
| Calcium hydroxide | Starting material | Starting material | Partially crystalline |
| N,N,N-Trimethylglycine | Starting material | Starting material | Starting material |
| Ammonium hydroxide | Crystalline: Pattern 1 | Crystalline: Pattern 1 | Crystalline: Pattern 1 |
| Magnesium hydroxide | Starting material | Starting material | Starting material |
| Choline | Partially crystalline: Pattern 1 + starting material | Partially crystalline: Pattern 1 | Partially crystalline: Pattern 1 |
| Diethylamine | Crystalline: Pattern 1 | Crystalline: Pattern 2 | Crystalline: Pattern 1 + extra peak |
| L-Lysine | Starting material + extra peak | Crystalline: Pattern 1 | Partially crystalline |
| N,N'-Dibenzylethylenediamine | Crystalline: Pattern 1 | Crystalline: Pattern 1 | Crystalline: Pattern 1 |
| N-Ethylglucamine | Crystalline: Pattern 1 | Crystalline: Pattern 2 (similar to Pattern 1) | Partially crystalline: Pattern 2 |
| Calcium acetate | Crystalline: Pattern 1 | Starting material + extra peak | Partially crystalline: Pattern 2 |
| 1-(2-Hydroxyethyl)pyrrolidine | Oil | Oil | Oil |
| N-(Phenylmethyl)benzeneethaneamine | Crystalline: Pattern 1 | Crystalline: Pattern 2 (similar to Pattern 1) | Partially crystalline: Pattern 2 |
| Ammonia | Starting material | Starting material | Starting material |
| Magnesium acetate | Crystalline: Pattern 1 | Starting material + extra peaks | Partially crystalline: Pattern 2 |
| N-Methylglucamine | Crystalline: Pattern 1 | Crystalline: Pattern 1 | Crystalline: Pattern 1 |
| Tromethamine | Crystalline: Pattern 1 | Crystalline: Pattern 1 | Crystalline: Pattern 1 |
| 4-(2-Hydroxyethyl)morpholine | Crystalline: Pattern 1 | Crystalline: Pattern 1 | Crystalline: Pattern 1 |
| 2-(Diethylamino)ethanol | Oil | Oil | Oil |
| 2-Dimethylamino-ethanol | Oil | Oil | Oil |

Example 10: Aqueous Solubility

Aqueous solubility assessment was performed using Ca. 5 mg of each of the solids which had shown a unique pattern by XRPD. These samples were added to aliquots of deionized water up to a maximum of 4000 μL with the samples being shaken between additions to encourage dissolution prior to a visual inspection. It was observed that at room temperature none of the samples dissolved, however after shaking the samples overnight at 50° C. five samples were observed to have undergone complete dissolution and a further seven had partially dissolved.

Ca. 50 mg of each of the salts were weighed into a 2 mL HPLC vial prior to the addition of 1 mL of deionized water. The samples were then shaken for 24 h at 25° C. before being filtered into pre-weighed filter cartridges and dried overnight in vacuo and re-weighed, from this the solubility was calculated. The experiment was also repeated at 50° C. (see Table 4).

TABLE 4

Solubility assessment of selected samples from the salt screen

| Salt Former | From Ethanol | from DIPE | from MIBK |
| --- | --- | --- | --- |
| Potassium hydroxide | Complete dissolution at 50° C. | Complete dissolution at 50° C. | Partial dissolution at 50° C. |
| Sodium hydroxide | Complete dissolution at 50° C. | Complete dissolution at 50° C. | N/A |
| Ammonium hydroxide | Partial dissolution at 50° C. | N/A | N/A |

TABLE 4-continued

Solubility assessment of selected samples from the salt screen

| Salt Former | From Ethanol | from DIPE | from MIBK |
|---|---|---|---|
| Choline | N/A | N/A | No dissolution observed |
| Diethylamine | Partial dissolution at 50° C. | Complete dissolution at 50° C. | N/A |
| L-Lysine | N/A | Partial dissolution at 50° C. | N/A |
| N,N'-Dibenzylethyl-enediamine | N/A | N/A | No dissolution observed |

TABLE 4-continued

Solubility assessment of selected samples from the salt screen

| Salt Former | From Ethanol | from DIPE | from MIBK |
|---|---|---|---|
| N-Ethylglucamine | Partial dissolution at 50° C. | Partial dissolution at 50° C. | N/A |
| Calcium acetate | No dissolution observed | N/A | N/A |
| N-(Phenylmethyl)benzeneethaneamine | No dissolution observed | No dissolution observed | N/A |
| Magnesium acetate | No dissolution observed | N/A | N/A |
| N-Methylglucamine | Partial dissolution at 50° C. | N/A | N/A |
| Tromethamine | No dissolution observed | N/A | N/A |
| 4-(2-hydroxyethyl)-morpholine | N/A | N/A | No dissolution observed |

Example 11: 1H Nuclear Magnetic Resonance Spectroscopy (NMR)

Samples for NMR analysis were prepared by weighing 5-7 mg of sample into a 1.5 mL HPLC vial prior to dissolving in d-DMSO, the samples were then transferred to field matched 5 mm NMR tubes for analysis. Analysis of the samples was performed using the standard instrument settings.

1H NMR data for the completely soluble or partially soluble salts prepared during the screen showed all to have different chemical shifts for peaks associated with protons around the carboxylate group compared to that of the free acid. This is indicative of salt formation (peaks at 9.91, 8.22 4.38 and 4.03 of the free acid Compound 1 show the most significant changes in shifts, see Table 5. Several samples also showed solvent present in the NMRs which could either be the result of insufficient drying or the formation of solvates; water was also seen in all NMR data, however this may be preparation-related. In cases where the counter ion was visible by 1H NMR it has also been quantified (See Table 5).

TABLE 5

$^1$H NMR analysis

| Salt Former | $^1$H NMR Analysis |
|---|---|
| Potassium hydroxide | 11.82(s, 1H), 7.89(s, 1H), 7.48(d, 2H, J = 8.0 Hz), 7.37~7.18(m, 7H), 4.23(t, J = 8.0 Hz, 2H), 3.86(s, 2H), 3.05(t, J = 8.0 Hz, 2H). |
| Sodium hydroxide | 11.54(s, 1H), 7.93 (s, 1H), 7.48(d, 2H, J = 8.0 Hz), 7.37~7.18(m, 7H), 4.26(m, 2H), 3.89(s, 2H), 3.05(m, 2H). |
| Ammonium hydroxide | 11.40(s, 1H), 7.96(s, 1H), 7.42(d, 2H, J = 4.8 Hz), 7.21(m, 7H), 4.26(m, 2H), 3.88(s, 2H), 3.06(m, 2H). |
| Diethylamine | 11.34(s, 1H), 7.98(s, 1H), 7.48(d, 2H, J = 8.0 Hz), 7.21(m, 7H), 4.28(m, 2H), 3.90(s, 2H), 3.31(bs, 4H), 3.07(m, 2H), 2.90(m, 4H), 1.18(t, J = 8.0 Hz, 6H). |
| L-Lysine | 7.85(s, 1H), 7.42(m, 2H), 7.40-7.12(m, 7H), 4.17(t, J = 8.0 Hz, 2H), 3.81(s, 2H), 3.08(m, 3H), 2.99(m, 3H), 2.69(m, 2H), 1.80~1.40(m, 4H). |
| N-Ethylglucamine | 7.85(s, 1H), 7.42(m, 2H), 7.40~7.12(m, 7H), 4.17(t, J = 8.0 Hz, 2H), 3.81(s, 2H), 3.08(m, 3H), 2.99(m, 3H), 2.69(m, 2H), 1.80~1.40 (m, 4H). |
| N-Methylglucamine | 7.85(s, 1H), 7.42(m, 2H), 7.40~7.12(m, 7H), 4.17(t, J = 8.0 Hz, 2H), 3.81(s, 2H), 3.08(m, 3H), 2.99(m, 3H), 2.69(m, 2H), 1.80~1.40 (m, 4H). |

Example 12: Differential Scanning Calorimetry (DSC)

Ca. 1-3 mg of sample was placed onto a pre-weighed aluminium DSC pan using an analytical balance. The sample was heated from RT to Ca. 5° C. higher than the degradation point at 10° C./min under a nitrogen atmosphere. Each of the data sets were examined for any thermal events.

Example 13: Fourier Transform Infrared Spectroscopy (FT-IR)

Ca. 1-2 mg of sample was placed on to the crystal of the ATR module and secured into position. All the data generated was modified by removal of the background within the analysis software.

Example 14: Polarised Light Microscopy (PLM)

Samples were prepared on glass microscope slides using 1-2 drops of immersion oil and a glass cover slip. Optical assessment of the samples was performed using an appropriate objective lens with the polarizers being in the crossed, partially crossed and uncrossed positions.

Example 15: Hot-Stage Microscopy (HSM)

Samples were prepared on glass microscope slides and heated at 10° C./min to mimic the temperature profiles used with the TGA and DSC, up to the samples' melting point after which they were cooled to room temperature without forced cooling.

Example 16: Dynamic Vapor Sorption (DVS)

Ca. 10-15 mg of sample was weighed into a stainless steel DVS basket before submitting for analysis. The samples were analysed over the range of 0-90% RH with a maximum time of 6 hours per humidity stage. Each sample was exposed to a double cycle. XRPD analysis of all samples was performed post-DVS.

Example 17: Thermo Gravimetric Analysis (TGA)

The samples were heated from RT to 400° C. at 10° C./min (unless otherwise stated) under a stream of nitrogen gas. Each of the data sets were examined to determine mass losses and the degradation temperature of the samples.

Example 18: Inductively Coupled Plasma (ICP)

Ca. 0.10 g of test sample was digested in 5 mL nitric acid and made to volume with deionized water. The test sample was then diluted further and analyzed against a set of calibration standards to determine the sodium and potassium content.

Example 19: Karl Fischer

Ca. 0.05 g of test sample was back weighed into the KF vessel and titrated with Hydranal® Composite 5 to determine the % water content of the salt.

Example 20: Particle Size

Dispersant: Air, Lens: R3 (potassium and diethylamine) & R5 (sodium), Pressure: 4 bar, Feed velocity: 40 mm/s, Optical model: Fraunhofer, Measurement time: 5 seconds, Samples were analyzed as dry powders in duplicate with an average of the values recorded being reported.

Example 21: HPLC

Flow rate: 3.03 mL/min, Method: Isocratic, Column temperature: 25° C., Wavelength range: 190-400 nm, Solvent A: 25 mM Ammonium acetate buffer—pH 5.5 (30%), Solvent B: MeOH (70%), Injection volume: 15 μL, Run time: 20 minutes.

Example 22: FaSSIF/FeSSIF/Solubility

Ca. 25 mg of each of the salts were weighed into a 2 mL HPLC vial prior to the addition of 1 mL of Fasting State Simulated Intenstinal Fluid (FaSSIS) solution. The samples were then shaken for 24 h at 37° C. before being filtered into pre-weighed filter cartridges and dried overnight in vacuo and re-weighed, from this the solubility was calculated. The experiment was also repeated using Fed State Simulated Intestinal Fluid (FeSSIF) solution.

Example 23: pH1 Stability

Ca. 25 mg of each of the salts were weighed into a 2 mL HPLC vial prior to the addition of 1 mL of pH 1 buffer. The samples were then shaken for 4 h at 37° C. before being filtered into SPE cartridges and dried overnight.

Example 24: pH

A saturated solution of each of the salts was prepared in 5 mL of deionized water at room temperature prior to analysis.

TABLE 6

| Technique | Result |
|---|---|
| \multicolumn{2}{c}{Summary of characterization of potassium salt} | |
| Yield | 93.5% |
| Appearance | White powder |
| XRPD | Partially crystalline-new pattern. The experimental conditions were selected from the salt screen to give XRPD pattern 2; since pattern 2 was not observed this might indicate polymorphism. |
| $^1$H NMR | Chemical shifts and loss of proton at ionizable center indicating salt formation had occurred. Water and a trace amount of DIPE were also observed. |
| PLM | Birefringent needles and lathes up to 100 μm in length |
| HSM | Loss of birefringence observed between 116-129° C., shrinkage/change in structure of particles observed between 153-161° C., melt observed between 189-210° C. and on cooling re-crystallisation occurred between 198-182° C. |
| TGA | 1 × mass loss prior to decomposition between 25-170° C. (4.8%) loss of water, decomposition occurred at >225° C. |
| DSC | 3 × endotherms with onsets at 111.6° C. (loss of water), 147° C. (initial melt) and 186° C. (secondary melt). Since no re-crystallisation was observed between melts this may indicate a mix of crystalline phases. |
| FT-IR | Reference trace: closely matches the pattern of the sodium salt |
| Particle size (dry powder) | X10: Average: 1.61, StdDev: 0.04, % RSD: 2.20 X50: Average: 6.48, StdDev: 0.35, % RSD: 5.46 X90: Average: 35.09, StdDev: 1.82, % RSD: 5.18 VMD: Average: 13.07, StdDev: 0.62, % RSD: 4.71 |
| DVS | Ca. 5.7% mass increase between 0-90% RH on the first cycle and Ca. 4.7% mass increase on the second cycle. Between Ca. 10-50% RH hysteresis was observed. The change in sample mass observed between the $1^{st}$ and $2^{nd}$ cycles may indicate a change in form. |

TABLE 6-continued

Summary of characterization of potassium salt

| Technique | Result |
| --- | --- |
| XRPD post DVS | Partially crystalline-pattern is different from free acid indicating a novel polymorphic form. |
| Karl Fischer | 5.78% Water, 1:1.6 (salt: water), suggesting the material is a sesiqu-hydrate |
| ICP | 8.03% Potassium (1:0.95 API : potassium counter ion) |
| Chemical purity (HPLC) | >99.9% (by peak area) |
| Aqueous solubility @ 25° C. | 6.6 mg/mL |
| Aqueous solubility @ 50° C. | 16.2 mg/mL |
| FaSSIF solubility @ 37° C. | 1.5 mg/mL |
| FeSSIF solubility @ 37° C. | 1.6 mg/mL |
| Observation post stability (40° C./75% RH) | No visible change |
| XRPD post stability (40° C./75% RH) | Partially crystalline-no change in form |
| Chemical purity post stability (40° C./75% RH) | >99.9% (by peak area) |
| Observations post stability (pH 1 for 4 h) | No visual change |
| XRPD post stability (pH 1 for 4 h) | Partially crystalline: change in crystalline form compared to the free acid |
| Chemical purity post stability (pH 1 for 4 h) | >99.9% (by peak area) |
| $^1$H NMR post stability (pH 1 for 4h) | Reduction in chemical shifts, indicating that salt form is no longer present. Water also present. |
| pH of rm temp sat'd sol'n | 9.21 |

TABLE 7

Summary of characterization of sodium salt

| Technique | Result |
| --- | --- |
| Yield | 101.3% |
| Appearance | White powder |
| XRPD | Crystalline - matches the pattern of the sodium salt prepared from DIPE |
| $^1$H NMR | Chemical shifts and loss of proton at carboxylate, indicating salt formation had occurred. Water was also observed. |
| PLM | Typically the sample is comprised of agglomerates of birefringent needles up to 20 μm in length. |
| HSM | The sample was observed to melt between 98-123° C. and on cooling re-crystallisation occurred between 134-132° C. |
| TGA | 1× mass loss prior to decomposition between 25-80° C. (7.7%) - loss of water, decomposition occurred at >240° C. |
| DSC | 2× endotherms with onsets at 157.5° C. (initial melt) and 159.9° C. (secondary melt). Since no re-crystallisation was observed between melts this may indicate a mix of crystalline phases. |
| FT-IR | Reference trace: closely matches the pattern of the potassium salt |
| Particle size (dry powder) | X10: Average: 6.40, StdDev: 0.33, % RSD: 5.20<br>X50: Average: 118.75, StdDev: 5.88, % RSD: 4.95<br>X90: Average: 304.01, StdDev: 22.91, % RSD: 7.54<br>VMD: Average: 140.17, StdDev: 9.09, % RSD: 6.48 |
| DVS | Ca. 11.7% mass increase between 0-90% RH on each cycle. Between Ca. 50-80% RH hysteresis was observed. Between 0-10% there was a mass increase of Ca. 6.5-6.7% (ca. 1.7 eq water) which indicates a hydrate formation. |
| XRPD post DVS | Crystalline - no change in form |
| Karl Fischer | 7.03% Water, 1:1.9 (salt:water), this suggest the material is a di-hydrate |
| ICP | 6.22% Sodium (1:1.24 API:sodium counter ion) |
| Chemical purity (HPLC) | >99.9% (by peak area) |
| Aqueous solubility @ 25° C. | 2.3 mg/mL |
| Aqueous solubility @ 50° C. | 2.4 mg/mL |
| FaSSIF solubility @ 37° C. | 4.0 mg/mL |
| FeSSIF solubility @ 37° C. | 3.8 mg/mL |
| Observation post stability (40° C./75% RH) | No visible change |
| XRPD post stability (40° C./75% RH) | Crystalline - no change in form |
| Chemical purity post stability (40° C./75% RH) | >99.9% (by peak area) |
| Observations post stability (pH 1 for 4 h) | No visual change |
| XRPD post stability (pH 1 for 4 h) | Partially crystalline: change in crystalline form to that of the free acid |
| Chemical purity post stability (pH 1 for 4 h) | >99.9% (by peak area) |
| $^1$H NMR post stability (pH 1 for 4 h) | No chemical shifts, indicating that salt form is no longer present. Water also present. |
| pH of rm temp sat'd sol'n | 10.31 |

TABLE 8

| Summary of characterization of diethylamine salt | |
| --- | --- |
| Technique | Result |
| Yield | 92.6% |
| Appearance | White powder |
| XRPD | Crystalline-Pattern 1. The experimental conditions used should have prepared the Pattern 2 diethylamine salt as generated during the salt screen, this indicates Pattern 1 may be a more stable form. |
| $^1$H NMR | Chemical shifts and loss of proton at ionizable centre indicating salt formation had occurred. Diethylamine was present in a ratio of 1:1.0 (API to counter ion). Water was also observed. |
| PLM | The sample is comprised of birefringent lathes up to 50 μm in length with agglomerates. |
| HSM | Particle movement observed between 72-145° C. prior to an initial melt between 145-154° C., a secondary melt was observed between 199-209° C., re-crystallisation occurred on cooling between 117-84° C. |
| TGA | 2 x mass loss prior to decomposition between Ca. 110-165° C. (5.5%) and 165-290° C. (17.6%) these mass losses could be loss of counter ion. Decomposition occurred at >290° C. |
| DSC | 1 x endotherm with an onset at 214.5° C. (melt). A base line shift/broad endotherm is also observed between 85-130° C. which could be due to the dissociation of the counter ion-this would indicate instability of the salt form above 85° C. |
| FT-IR | Reference trace: pattern is dissimilar to the other salts prepared indicating a different structural arrangement |
| Particle size (dry powder) | X10: Average: 1.62, StdDev: 0.04, % RSD: 2.62<br>X50: Average: 6.06, StdDev: 0.12, % RSD: 1.99<br>X90: Average: 15.94, StdDev: 0.62, % RSD: 3.86<br>VMD: Average: 7.86, StdDev: 0.34, % RSD: 4.32 |
| DVS | Ca. 0.1% mass increase between 0-90% RH on the first cycle and second cycles. No significant hysteresis was observed during the experiment |
| XRPD post DVS | Crystalline-no change in form |
| Karl Fischer | 0.21% water, 1:0.1 (salt:water)-this shows the sample is anhydrous |
| Chemical purity (HPLC) | >99.9% (by peak area) |
| Aqueous solubility @ 25° C. | 5.1 mg/mL |
| Aqueous solubility @ 50° C. | 9.2 mg/mL |
| FaSSIF solubility @ 37° C. | 1.3 mg/mL |
| FeSSIF solubility @ 37° C. | 0.1 mg/mL |
| Observation post stability (40° C./75% RH) | No visible change |
| XRPD post stability (40° C./75% RH) | Crystalline-no change in form |
| Chemical purity post stability (40° C./75% RH) | >99.9% (by peak area) |
| Observations post stability (pH 1 for 4 h) | No visual change |
| XRPD post stability (pH 1 for 4 h) | Partially crystalline: change in crystalline form from that of free acid |
| Chemical purity post stability (pH 1 for 4 h) | >99.9% (by peak area) |
| $^1$H NMR post stability (pH 1 for 4 h) | Reduction in chemical shifts, indicating that salt form is no longer present. Water also observed. |
| pH of rm temp sat'd sol'n | 8.08 |

Formulations

The salts Formulae 2 disclosed are not stable under acidic conditions, and therefore formulations for clinical use should be prepared with suitable buffering and/or coating so as to survive under the conditions in the stomach (e.g. an "enteric coated" formulation), or so as to be administered by other than an oral route (e.g. by injection or patch).

Preparing the salts Formulae 2 in dosage forms for oral administration, injection, administration by trans-dermal patch and the like, including excipients such as flavorings, buffers, carriers and the like, and packaging of the dosage forms are considered to be within the skill of the ordinary artisan. See, e.g. Remington: the Science and Practice of Pharmacy, 22nd Ed., c. 2013 by Pharmaceutical Press, hereby incorporated by reference in its entirety and for all purposes. The formulations should be prepared and administered so as to provide a dose in the range from 1-1000 mg/day to a subject, or to provide a dose range from 1-100 mg/day to a subject, or a dose range from 10-100 mg/day to a subject.

What is claimed is:

1. A salt compound having the formula (2):

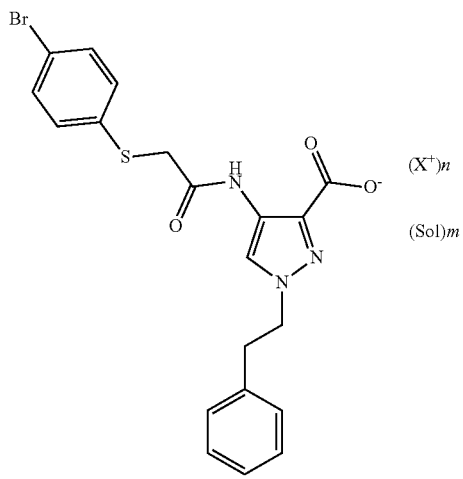

Formula 2 wherein:
n is 1, 2 or 3;
m is 0, 0.5, 1, 2 or 3;
$X^+$ is a cation of potassium, sodium, choline, diethylamine, dimethylamine, L-lysine, N,N'-dibenzylethylenediamine, N-ethylglucamine, 1-(2-hydroxyethyl)pyrrolidine, N-(phenylmethyl)benzeneethaneamine, ammonia, N-methylglucamine, tromethamine, 4-(2-hydroxyethyl)morpholine, 2-(diethylamino)ethanol, or 2-dimethylamino-ethanol; and
Sol is a solvent molecule that is water or an organic solvent selected from among 1,1-dimethoxyethane, 1,2-dichloroethane, benzonitrile, ethyl acetate, 1,4-dioxane, anisole, heptane, 2-butanol, cumene, hexane, 2-propanol, cyclohexane, isopropyl acetate, 4-methyl-pentan-2-one, dichloromethane, diisopropyl ether (DIPE), isobutyl acetate, tetralin, toluene, methylethyl ketone (MEK), N-methylpyrrolidone, tert-butylmethyl ether (TMBE), nitromethane, pyridine or tetrahydrofuran, methanol, ethanol, acetone or acetonitrile, or any two or three of them.

2. The salt compound of claim 1 in which $X^+$ is potassium ion, sodium ion or quaternary dimethylamine or quaternary diethylamine.

3. The salt compound of claim 1, in which m is 0.5 or 1.

4. The salt compound of claim 2, in which m is 0.5 or 1.

5. The salt compound of claim 1, wherein the solvent is 4-methyl-pentan-2-one, ethanol or diisopropyl ether.

6. The salt compound of claim 2, wherein the solvent is ethanol or diisopropyl ether.

7. A process for preparing the salt compound of Formula 2:

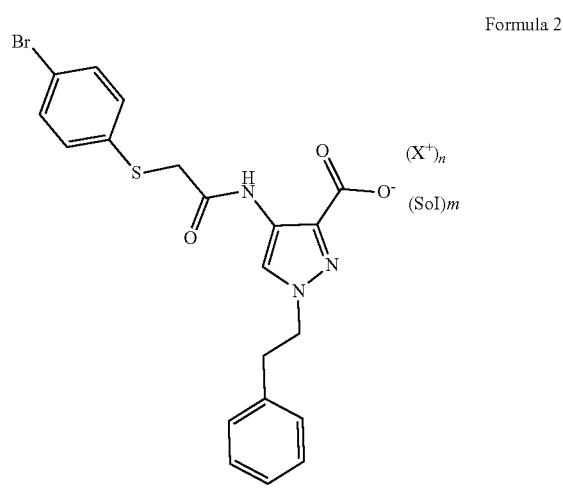

Formula 2 wherein:
n is 1, 2 or 3;
m is 0, 0.5, 1, 2 or 3;
$X^+$ is a cation of potassium, a sodium, choline, diethylamine, dimethylamine, L-lysine, N,N'-dibenzylethylenediamine, N-ethylglucamine, 1-(2-hydroxyethyl) pyrrolidine, N-(phenylmethyl) benzeneethaneamine, ammonia, N-methylglucamine, tromethamine, 4-(2-hydroxyethyl) morpholine, 2-(diethylamino)ethanol, or 2-dimethylamino-ethanol; and
Sol is a solvent molecule that is methanol, ethanol, acetone, acetonitrile, 1,1-dimethoxyethane, 1,2-dichloroethane, benzonitrile, ethyl acetate, 1,4-dioxane, anisole, heptane, 2-butanol, cumene, hexane, 2-propanol, cyclohexane, isopropyl acetate, 4-methyl-pentan-2-one, dichloromethane, diisopropyl ether (DIPE), isobutyl acetate, tetralin, toluene, methylethyl ketone (MEK), N-methylpyrrolidone, tert-butylmethyl ether (TMBE), nitromethane, pyridine, tetrahydrofuran or water, or a mixture of any two or three of them, the process comprising:
i) dissolving the free acid form of a compound of formula 2 in an organic solvent that is selected from among methanol, ethanol, acetone, acetonitrile, 1,1-dimethoxyethane, 1,2-dichloroethane, benzonitrile, ethyl acetate, 1,4-dioxane, anisole, heptane, 2-butanol, cumene, hexane, 2-propanol, cyclohexane, isopropyl acetate, 4-methyl-pentan-2-one, dichloromethane, diisopropyl ether (DIPE), isobutyl acetate, tetralin, toluene, methylethyl ketone (MEK), N-methylpyrrolidone, tert-butylmethyl ether (TMBE), nitromethane, pyridine or tetrahydrofuran, or a mixture of any two or three of them, or in said organic solvent mixed with water;

ii) adding an excess over the stoichiometric amount of a base of sodium, potassium, choline, diethylamine, dimethylamine, L-lysine, N,N'-dibenzylethylenediamine, N-ethylglucamine, 1-(2-hydroxyethyl)pyrrolidine, N-(phenylmethyl)benzeneethaneamine, ammonia, N-methylglucamine, tromethamine, 4-(2-hydroxyethyl)morpholine, 2-(diethylamino)ethanol, or 2-dimethylamino-ethanol required to titrate the free acid compound of formula 2 to form a precipitate of the salt compound of formula 2; and iii) collecting the precipitate to obtain the salt compound 2.

8. The process of claim 7, in which the organic solvent is ethanol or diisopropyl ether (DIPE) or 4-methyl-pentan-2-one.

9. The process of claim 7, in which the base is sodium hydroxide, potassium hydroxide or a salt of quaternary dimethylamine or a salt of quaternary diethylamine.

10. The process of claim 8, in which the base is sodium hydroxide, potassium hydroxide or a salt of quaternary dimethylamine or a salt of quaternary diethylamine.

11. The process of claim 7, in which the solvent is water mixed with a polar organic solvent.

12. The process of claim 11, in which the ratio of water to polar organic solvent ranges from 5:1 to 10:0.1.

13. The process of claim 8, in which the solvent is water mixed with a polar organic solvent.

14. The process of claim 13, in which the ratio of water to polar organic solvent ranges from 5:1 to 10:0.1.

15. The process of claim 9, in which the solvent is water mixed with a polar organic solvent.

16. The process of claim 15, in which the ratio of water to polar organic solvent ranges from 5:1 to 10:0.1.

* * * * *